(12) United States Patent
Sakurai et al.

(10) Patent No.: US 6,569,109 B2
(45) Date of Patent: May 27, 2003

(54) ULTRASONIC OPERATION APPARATUS FOR PERFORMING FOLLOW-UP CONTROL OF RESONANCE FREQUENCY DRIVE OF ULTRASONIC OSCILLATOR BY DIGITAL PLL SYSTEM USING DDS (DIRECT DIGITAL SYNTHESIZER)

(75) Inventors: Tomohisa Sakurai, Sagamihara (JP); Yoshitaka Honda, Tokorozawa (JP); Kazue Tanaka, Sagamihara (JP); Hiroo Ono, Hino (JP); Hiroyuki Takahashi, Akishima (JP)

(73) Assignee: Olympus Optical Co., Ltd., Tokyo (JP)

( * ) Notice: Subject to any disclaimer, the term of this patent is extended or adjusted under 35 U.S.C. 154(b) by 121 days.

(21) Appl. No.: 09/774,920

(22) Filed: Jan. 31, 2001

(65) Prior Publication Data

US 2001/0039389 A1 Nov. 8, 2001

(30) Foreign Application Priority Data

| | | |
|---|---|---|
| Feb. 4, 2000 | (JP) | 2000-028090 |
| Mar. 14, 2000 | (JP) | 2000-071159 |
| Jun. 5, 2000 | (JP) | 2000-167809 |
| Jun. 9, 2000 | (JP) | 2000-174088 |
| Aug. 2, 2000 | (JP) | 2000-234697 |
| Dec. 21, 2000 | (JP) | 2000-389387 |

(51) Int. Cl.[7] ............................... A61B 1/00
(52) U.S. Cl. ................. 601/2; 607/2; 606/27
(58) Field of Search ............... 600/437–472; 601/2; 607/2; 606/27

(56) References Cited

U.S. PATENT DOCUMENTS

| | | | |
|---|---|---|---|
| 4,794,933 A | * 1/1989 | Yamazaki | 600/455 |
| 4,965,532 A | 10/1990 | Sakurai | |
| 4,973,876 A | * 11/1990 | Roberts | 310/316.01 |
| 5,505,203 A | * 4/1996 | Deitrich et al. | 600/437 |
| 5,957,850 A | * 9/1999 | Marian et al. | 600/459 |

FOREIGN PATENT DOCUMENTS

| | | |
|---|---|---|
| JP | 2647713 | 5/1997 |
| JP | 2691011 | 8/1997 |

* cited by examiner

*Primary Examiner*—Francis J. Jaworski
*Assistant Examiner*—William C. Jung
(74) *Attorney, Agent, or Firm*—Scully, Scott, Murphy & Presser

(57) ABSTRACT

An ultrasonic driving apparatus consists mainly of a digital oscillatory circuit, an amplifier, a detection circuit, a phase difference detection circuit, a register, a data transfer circuit, and a switching circuit. The digital oscillatory circuit is used to drive an ultrasonic transducer at the resonance frequency of the ultrasonic transducer. The amplifier amplifies a driving signal output from the digital oscillatory circuit. The detection circuit detects the phase $\theta v$ of an applied voltage and the phase $\theta i$ of an induced current from the driving signal applied to the ultrasonic transducer via the amplifier. The phase difference detection circuit detects a difference between the phases $\theta v$ and $\theta i$. The register holds digital frequency data with which a frequency at which the digital oscillatory circuit is oscillated is determined, and changes the digital frequency data. The data transfer circuit transfers the digital frequency data to the register. The switching circuit is interposed between the phase difference detection circuit and register.

17 Claims, 21 Drawing Sheets

EQUIVALENT CIRCUIT OF ULTRASONIC TRANSDUCER

ULTRASONIC OPERATION APPARATUS FOR PERFORMING FOLLOW-UP CONTROL OF RESONANCE FREQUENCY DRIVE OF ULTRASONIC OSCILLATOR BY DIGITAL PLL SYSTEM USING DDS (DIRECT DIGITAL SYNTHESIZER)

This application claims benefit of Japanese Application No. 2000-028090 filed in Japan on Feb. 4, 2000, Japanese application No. 2000-071159 filed in Japan on Mar. 14, 2000, Japanese Application No. 2000-167809 filed in Japan on Jun. 5, 2000, Japanese Application No. 2000-174088 filed in Japan on Jun. 9, 2000, Japanese Application No. 2000-234697 filed in Japan on Aug. 2, 2000, and Japanese Application No. 2000-389387 filed in Japan on Dec. 21, 2000, the contents of which are incorporated by this reference.

BACKGROUND OF THE INVENTION

1. Field of the Invention

The present invention relates to an ultrasonic operation system, or more particularly, an ultrasonic operation system characterized by a control action of locking an output frequency on to the resonance frequency of an ultrasonic transducer so as to drive the ultrasonic transducer at the resonance frequency.

2. Related Art Statement

In general, an ultrasonic transducer employed in an ultrasonic knife for surgical use or in an ultrasonic aspirator should preferably be driven at the resonance frequency of the ultrasonic transducer or a frequency close to the resonance frequency. Among related arts, a known art is implemented in a driving apparatus including, for example, a phase-locked loop (PLL). In the driving apparatus, the phase of an induced current is compared with the phase of a driving voltage applied to the ultrasonic transducer, so that a driving frequency at which the ultrasonic transducer is driven will be agreed with the resonance frequency of the ultrasonic transducer.

This type of ultrasonic transducer is expressed as an equivalent circuit shown in FIG. 24 over a frequency band covering the resonance frequency that serves as a reference frequency. As illustrated, a coil Ld is connected in parallel or series with a braking capacitor Cd included in the ultrasonic transducer. Herein, the inductance of the coil Ld and the capacitance of the capacitor Cd have a relationship of L×C=Ld×Cd to the inductance of another coil L and the capacitance of another capacitor C to as to cancel the capacitance of the capacitor Cd. At the resonance frequency $fr=\frac{1}{2\pi}\sqrt{(L \times C)}(=\frac{1}{2\pi}(L'C)^{\frac{1}{2}})$, the property of the ultrasonic transducer is dominated by only a forward resistance of a resistor R. A phase difference between an applied voltage and an induced current becomes zero. FIG. 25 graphically shows an impedance Z offered by the ultrasonic transducer over a frequency band centered on the resonance frequency fr.

A PLL is activated in order to raise or lower a driving frequency, at which the ultrasonic transducer is driven, so that the phase difference between the phase θv of an applied voltage and the phase θi of an induced current will become zero. Consequently, a driving apparatus including the PLL is locked on to the resonance frequency fr. FIG. 26 shows the phase difference.

Herein, a frequency at which the driving apparatus is activated must fall within a range from a frequency f1 to a frequency f2 within which the driving apparatus can be locked on to the resonance frequency. Japanese Unexamined Patent Publication No. 2691011 has disclosed an improvement in which the frequency at which the driving apparatus is activated falls within the range.

FIG. 27 is an explanatory diagram concerning the disclosed related art. An ultrasonic operation system consists mainly of an ultrasonic transducer 1101, and a driving apparatus composed of a PLL 1102, an amplification circuit (AMP) 1103, a detection circuit 1104, an oscillatory circuit 1105, and a switch 1106. The ultrasonic transducer 1101 exhibits a resonance frequency of fr. The PLL 1102 tracks the resonance frequency according to the phase of a driving voltage applied to the ultrasonic transducer 1101 and the phase of an induced current. The amplification circuit 1103 amplifies the power of a frequency-change signal output from the PLL 1102 so as to produce driving power with which the ultrasonic transducer 1101 is driven. The detection circuit 1104 detects the applied voltage and induced current. The oscillatory circuit 1105 produces a reference-frequency signal that represents a reference frequency at which a driving apparatus is activated. The switch 1106 switches the connections of one input terminal of the PLL 1102 depending on whether the switch receives the induced current or reference-frequency signal. When the driving apparatus is activated, the reference-frequency signal (fref) output from the oscillatory circuit 1105 is input to the PLL 1102. Therefore, a voltage locked on to the reference frequency is applied to the ultrasonic transducer 1101. Thereafter, the connections of the one terminal of the PLL 1102 are switched in order to select the induced current as an input of the PLL 1102. Thus, the driving apparatus is locked on to the resonance frequency.

The reference-frequency signal produced by the oscillatory circuit 1105 is adjusted to fall within the frequencies f1 and f2. When the connections through the switch 1106 are changed, a driving frequency at which the ultrasonic transducer is driven falls within a frequency band within which the driving apparatus can be locked on to the resonance frequency. Therefore, the driving apparatus can reliably perform the action of locking the driving frequency on to the resonance frequency.

In an operation system including an ultrasonic knife, probes having various shapes are connected to an ultrasonic transducer and adopted for different purposes of use. Moreover, a plurality of types of ultrasonic transducers that exhibit different resonance frequencies may be used with employment of only one driving apparatus. In this case, handpieces each composed of a transducer and a probe exhibit different resonance frequencies. Consequently, a range from a frequency f1 to a frequency f2 within which a driving apparatus can be locked on to the resonance frequency of an ultrasonic transducer is different from handpiece to handpiece. A frequency at which the driving apparatus is activated is swept over a range covering the resonance frequency. Meanwhile, it is detected whether the frequency becomes equal to the resonance frequency. As soon as the frequency becomes equal to the resonance frequency, a PLL is activated to perform a phase locking action. This art is described in Japanese Patent Publication No. 2647713.

However, in the foregoing related art, a circuit for producing a frequency-change signal that represents a frequency at which the driving apparatus is activated and a PLL are of an analog type. It is therefore very hard to suppress an adverse effect caused by a difference of one product from another or to adjust each product. Moreover, when an additional probe or ultrasonic transducer is included, if a frequency at which the probe or ultrasonic transducer should be driven is unprecedented, a frequency setting circuit incorporated in the driving apparatus must be readjusted. This poses a problem.

Moreover, several digital resonance-frequency tracking circuits that are controlled by a CPU have been proposed in efforts to compensate for the drawbacks of the analog type. Since a tracking action depends on computation performed by software, the digital type has a drawback that a control action is performed slowly. If a fast CPU is employed in order to overcome the drawback, a driving apparatus itself becomes expensive. This poses a problem.

Furthermore, when the driving apparatus is applied to an ultrasonic operation system, it is important whether the driving apparatus can respond quickly when activated for oscillation. The driving apparatus must be designed to offer a high response speed.

OBJECTS AND SUMMARY OF THE INVENTION

Accordingly, an object of the present invention is to provide an ultrasonic driving apparatus capable of driving an ultrasonic transducer at a desired frequency more readily and accurately through digital signal processing, and an ultrasonic operation system.

Another object of the present invention is to provide an ultrasonic transducer driving apparatus capable of reliably locking a driving signal on to a resonance frequency even in a situation in which an impedance Z may rise spontaneously. Moreover, if an ultrasonic transducer is broken or any other abnormality occurs, the ultrasonic transducer driving apparatus can recognize the abnormality and stop operating.

Still another object of the present invention is to provide an ultrasonic coagulation/incision apparatus capable of reliably detecting whether the frequency of an induced current becomes equal to the resonance frequency of any of probes whose properties and use states are different from one another. The ultrasonic coagulation/incision apparatus can thus smoothly activate a PLL.

Still another object of the present invention is to provide an ultrasonic operation system capable of monitoring the frequency of an induced current within a frequency band covering the resonance frequency of each of a plurality of therapeutic appliances.

According to the present invention, an ultrasonic operation system consists mainly of a handpiece, a driving signal oscillator, an amplification circuit, a phase comparison circuit, and an arithmetic circuit. The handpiece includes an ultrasonic transducer that generates ultrasonic oscillations and is used to treat a living tissue using the ultrasonic oscillations. The driving signal oscillator includes a frequency data input unit that inputs digital frequency data, and produces a driving signal, based on which the ultrasonic transducer is driven, according to the digital frequency data. The amplification circuit amplifies the driving signal and outputs the resultant driving signal to the ultrasonic transducer. The phase comparison circuit compares the phase of a voltage applied based on the driving signal to the ultrasonic transducer with the phase of a current induced with the voltage. The arithmetic circuit calculates the digital frequency data according to the result of comparison performed by the phase comparison circuit.

Other features and advantages of the present invention will be fully apparent from the description below.

BRIEF DESCRIPTION OF THE DRAWINGS

FIG. 1 is a block diagram showing the configuration of an ultrasonic driving apparatus;

FIG. 2 is a flowchart describing the operations of the ultrasonic driving apparatus shown in FIG. 1;

FIG. 5 is a block diagram showing the configuration of an ultrasonic driving apparatus;

FIG. 6 is a flowchart describing the operations of the ultrasonic driving apparatus shown in FIG. 5;

FIG. 7 is an explanatory diagram concerning a frequency sweeping action included in the processing described in FIG. 6;

FIG. 9 to FIG. 11C are concerned with a sixth embodiment of the present invention;

FIG. 9 shows the configuration of an ultrasonic operation system;

FIG. 10 is a block diagram showing an ultrasonic coagulation/incision apparatus shown in FIG. 9;

FIG. 11A is a first explanatory diagram concerning the operations of a frequency change setting circuit shown in FIG. 10;

FIG. 11B is a second explanatory diagram concerning the operations of the frequency change setting circuit shown in FIG. 10;

FIG. 11C is a third explanatory diagram concerning the operations of the frequency change setting circuit shown in FIG. 10;

FIG. 15 shows the configuration of an ultrasonic operation system;

FIG. 16 is a block diagram showing the configuration of an ultrasonic coagulation/incision apparatus shown in FIG. 15;

FIG. 17 is a block diagram showing the configuration of a resonance frequency detection circuit shown in FIG. 16;

FIG. 18 is a flowchart describing the operations of the ultrasonic coagulation/incision apparatus shown in FIG. 16;

FIG. 19 shows the configuration of an ultrasonic operation system;

FIG. 20 is a block diagram showing the configuration of a main apparatus shown in FIG. 19;

FIG. 21 is a flowchart describing the operations of the main apparatus shown in FIG. 20;

FIG. 22 is a block diagram showing an ultrasonic transducer driving apparatus;

FIG. 23 shows waveforms for explaining wave data stored in a wave memory shown in FIG. 22;

FIG. 24 shows a typical electrically equivalent circuit of an ultrasonic transducer having a matching coil connected in parallel therewith;

FIG. 25 graphically shows an impedance offered by the equivalent circuit shown in FIG. 24;

FIG. 26 shows a relationship in phase between an applied voltage and an induced current over a frequency band including the resonance frequency of the ultrasonic transducer over which the ultrasonic transducer is driven; and FIG. 27 is a block diagram showing the configuration of a conventional ultrasonic driving apparatus.

DETAILED DESCRIPTION OF THE PREFERRED EMBODIMENTS

First Embodiment:

(Constituent Features)

Figure 1:
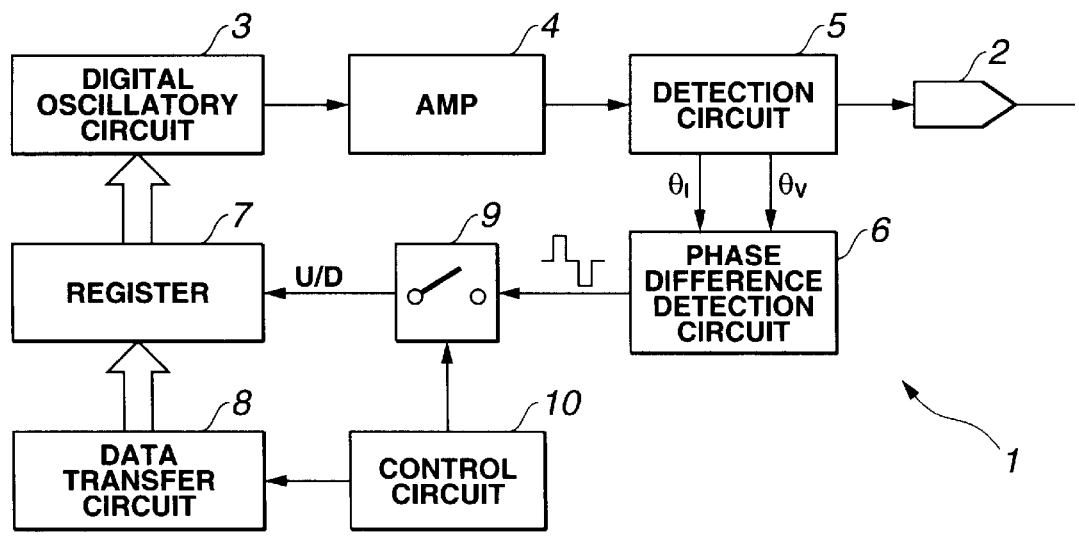
FIG. 1 and FIG. 2 are concerned with a first embodiment of the present invention.

An ultrasonic driving apparatus 1 in accordance with the present embodiment consists mainly of, as shown in FIG. 1, a digital oscillatory circuit 3, an amplification circuit (AMP) 4, a detection circuit 5, a phase difference detection circuit 6, a register 7, a data transfer circuit 8, a switching circuit 9, and a control circuit 10. The digital oscillatory circuit is realized with, for example, a direct digital synthesizer that is a digital circuit for producing a driving signal based on which an ultrasonic transducer 2 is driven at its resonance frequency. The amplification circuit 4 amplifies the driving signal output from the digital oscillatory circuit 3. The detection circuit 5 detects the phase θv of an applied voltage and the phase θi of an induced current as a feedback from the driving signal applied to the ultrasonic transducer 2 via the amplification circuit 4. The phase difference detection circuit 6 detects a difference between the phase θv of the applied voltage and the phase θi of the induced current that are output as the feedback from the detection circuit 5. The register 7 holds digital frequency data that determines an oscillatory frequency at which the digital oscillatory circuit 3 is oscillated. The register 7 can change the digital frequency data in response to an external signal. The data transfer circuit 8 transfers the digital frequency data, which represents the resonance frequency fr of the ultrasonic transducer 2 or a frequency close to the resonance frequency, to the register 7. The switching circuit 9 is interposed between the phase difference detection circuit 6 and register 7. The control circuit 10 controls the actions of the switching circuit 9 and data transfer circuit 8.

Herein, the ultrasonic transducer 2 can be adapted to a handpiece to be included in an ultrasonic operation system.

(Operations)

Figure 2:
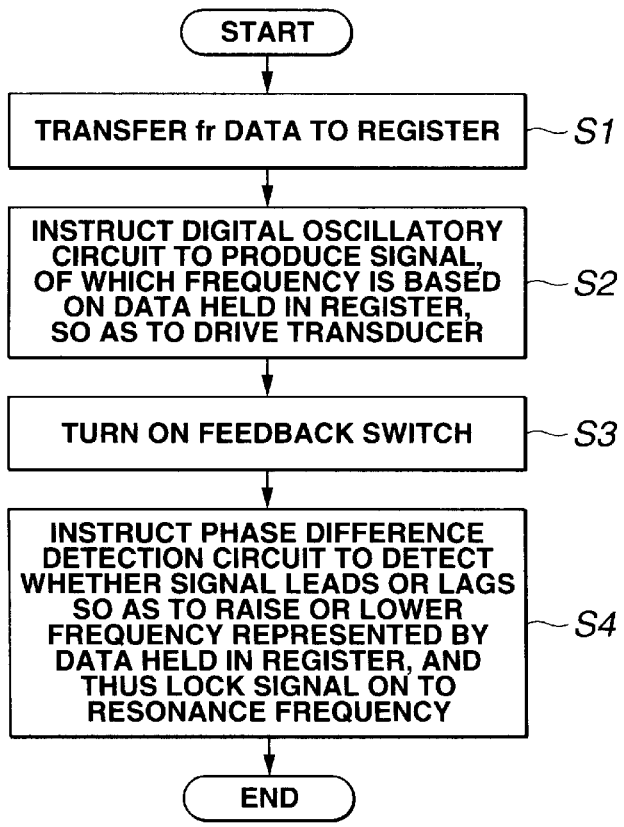

In the foregoing configuration, the control circuit 10 performs processing described in FIG. 2. Specifically, when the driving apparatus is activated for oscillation at step S1, the control unit 10 instructs the data transfer circuit 8 to transfer digital frequency data to the register 7 with the switching circuit 9 broken. At step S2, the oscillatory frequency at which the digital oscillatory circuit 3 is oscillated is substantially agreed with the resonance frequency fr of the ultrasonic transducer 2.

A driving signal whose frequency is identical or close to the resonance frequency fr of the ultrasonic transducer 2, which is regarded as a reference frequency, is applied to the ultrasonic transducer 2. Consequently, the detection circuit 5 detects an output very close to a feedback acquired when the ultrasonic transducer 2 is driven at its resonance frequency. That is to say, the detection circuit 5 detects the phase of an induced current and the phase of an applied voltage.

Figure 9:
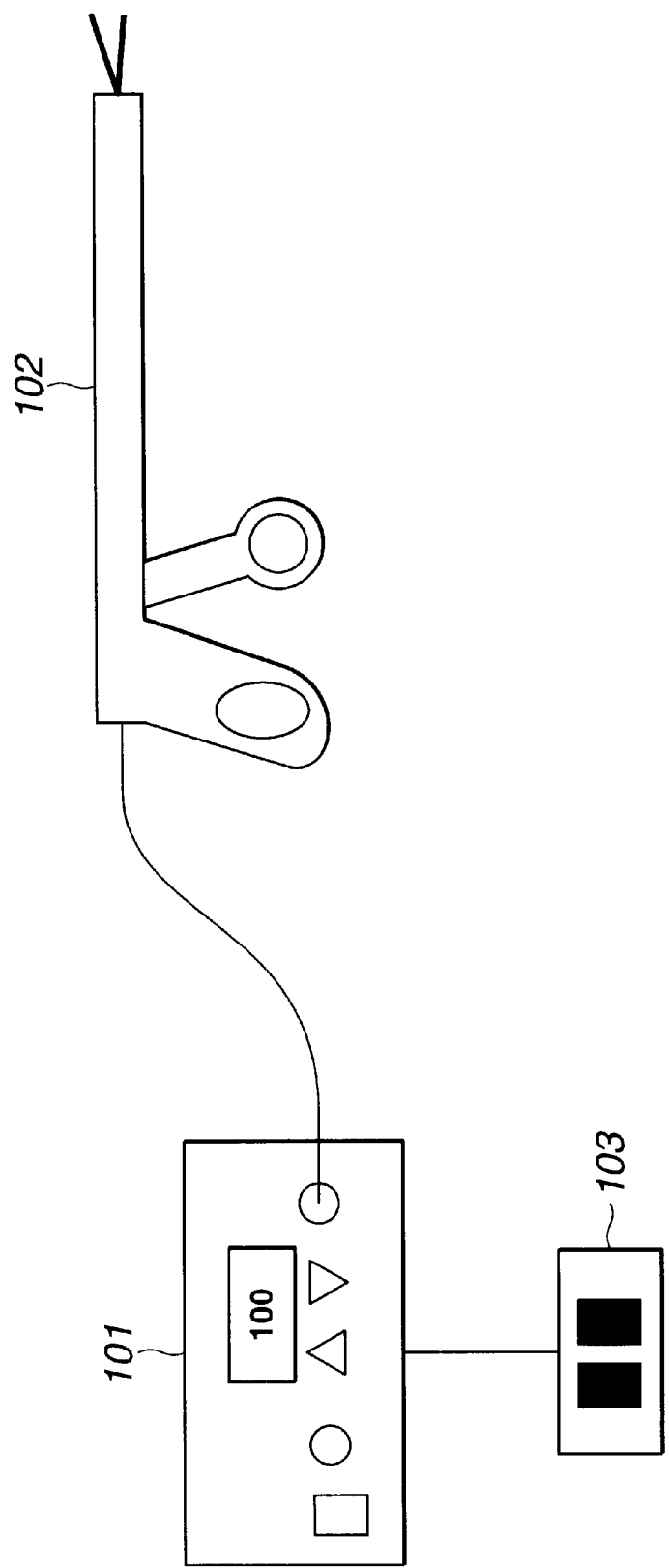
Figure 10:
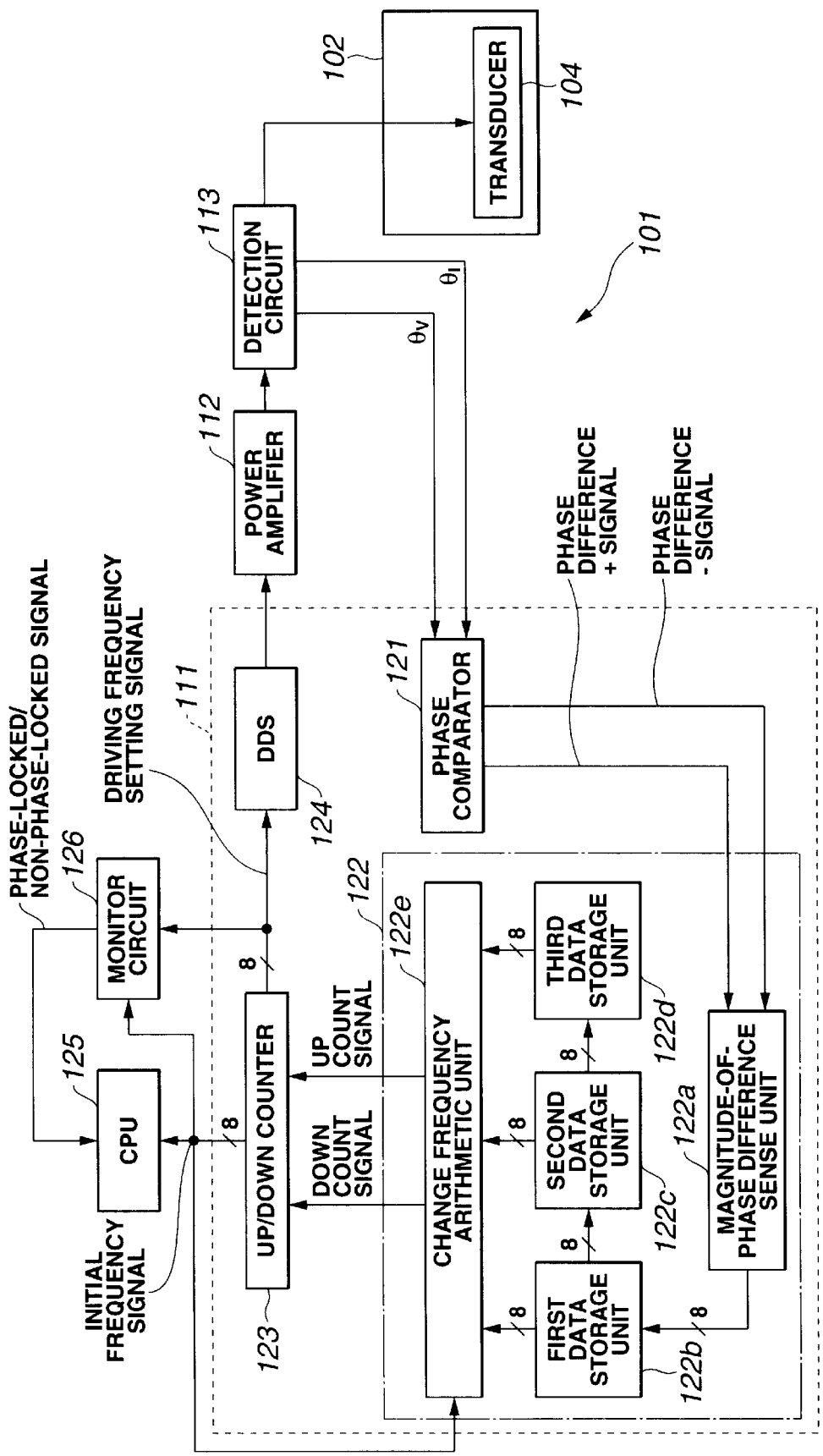
Figure 11:
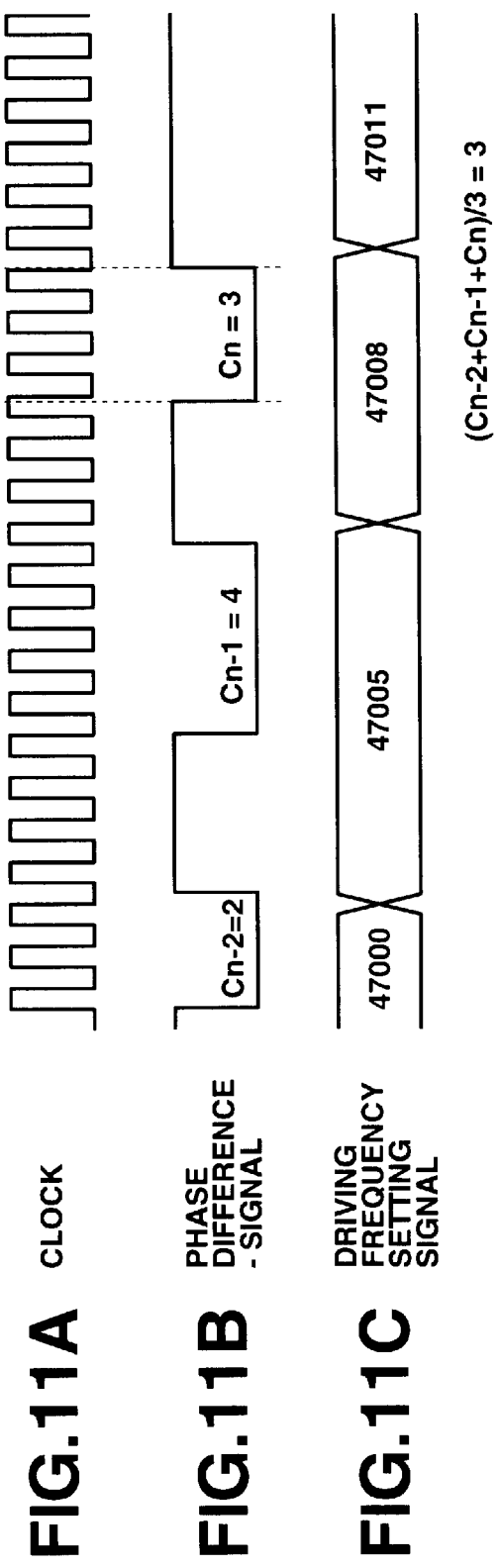

Referring to FIG. 9 to FIG. 11, the feedback will be described. FIG. 9 shows a typical electrically equivalent circuit of the ultrasonic transducer having a matching coil connected in parallel therewith. In general, the resonance frequency fr of an ultrasonic transducer is expressed as $fr = \frac{1}{2}\pi\sqrt{(L \times C)}$ ($=\frac{1}{2}\pi(L \times C)^{1/2}$).

For efficiently driving an ultrasonic transducer, a coil Ld is connected in series or parallel with the ultrasonic transducer. The coil Ld is set to balance with a braking capacitor Cd included in the ultrasonic transducer so that resonance can be attained. In other words, the coil Ld and capacitor Cd are set to an inductance and a capacitance respectively that satisfy $fr = \frac{1}{2}\pi\sqrt{(Ld \times Cd)}$. FIG. 10 shows an impedance offered by the equivalent circuit. Frequencies f1 and f2 are antiresonant frequencies. At the resonance frequency fr that is regarded as a reference frequency, the impedance assumes a minimum value R, and a phase difference between an applied voltage and an induced current is zero. At this time instant, electric energy supplied to the ultrasonic transducer is entirely consumed by a resistive component R, or in other words, converted into oscillatory energy.

FIG. 11 shows a relationship in phase between the applied voltage and induced current over a frequency band centered on the resonance frequency. As apparent from the drawing, when a driving frequency at which the ultrasonic transducer is driven is lower than the resonance frequency fr, the current lags behind the voltage. When the driving frequency is higher, the current leads. From this viewpoint, the driving frequency is adjusted based on a phase difference between the voltage and current. Consequently, even if the resonance frequency fr of the ultrasonic transducer is varied because of a load variation or a temperature change, the driving frequency can be changed between the frequencies f1 and f2 and locked on to the resonance frequency of the ultrasonic transducer. The ultrasonic transducer is thus always driven at the resonance frequency thereof.

Referring back to FIG. 2, after the detection circuit 5 detects a feedback composed of the phase of an induced current and the phase of an applied voltage, that is, after the ultrasonic transducer 2 is activated, the control circuit 10 brings the switching circuit 9 to a conducting state at step S3. At step S4, the feedback (U/D) is placed in the register 7 so that a frequency represented by the digital frequency data held in the register 7 can be raised or lowered according to a difference between the phase θv of the applied voltage and the phase θi of the induced current. Consequently, the oscillatory frequency of the digital oscillatory circuit 3 is changed, and a PLL action is performed digitally.

(Advantage)

As mentioned above, when the ultrasonic driving apparatus 1 of the present embodiment is activated, the digital oscillatory circuit 3 is oscillated based on digital frequency data that represents a frequency identical to or close to the resonance frequency fr of the ultrasonic transducer 2. Thereafter, the feedback (U/D) is placed in the register 7, and the frequency represented by the digital frequency data held in the register 7 is raised or lowered based on the difference between the phase θv of the applied voltage and the phase θi of the induced current that are fed to the phase difference detection circuit 6. The oscillatory frequency of the digital oscillatory circuit 3 is then changed. The driving signal to be applied to the ultrasonic transducer 2 is therefore adjusted. Consequently, the ultrasonic transducer 2 is driven exactly at the resonance frequency fr thereof.

If the frequency data sent from the data transfer circuit 8 represents a frequency that is equal to or lower than the frequency f1 or equal to or higher than the frequency f2, it is impossible from the beginning that a frequency adjustment mechanism composed of the aforesaid means locks the digital oscillatory circuit on to the resonance frequency fr using the feedback acquired when the driving apparatus is activated. In this case, the frequency data sent from the data transfer circuit 8 is modified to represent a frequency close to the resonance frequency fr, and then transferred to the register 7. Thus, the frequency of the driving signal produced by the digital oscillatory circuit 3 is approximated to the resonance frequency fr. Consequently, the digital oscillatory circuit is locked on to the resonance frequency.

Second Embodiment:

A second embodiment is nearly identical to the first embodiment. A difference alone will be described below. The same reference numerals will be assigned to components identical to those of the first embodiment, and the description of the components will be omitted.

(Constituent Features)

The second embodiment is configured to provide digital frequency data that represents the resonance frequency of an employed one of ultrasonic transducers 2a, 2b, and 2c that exhibit different resonance frequencies fr.

Figure 3:
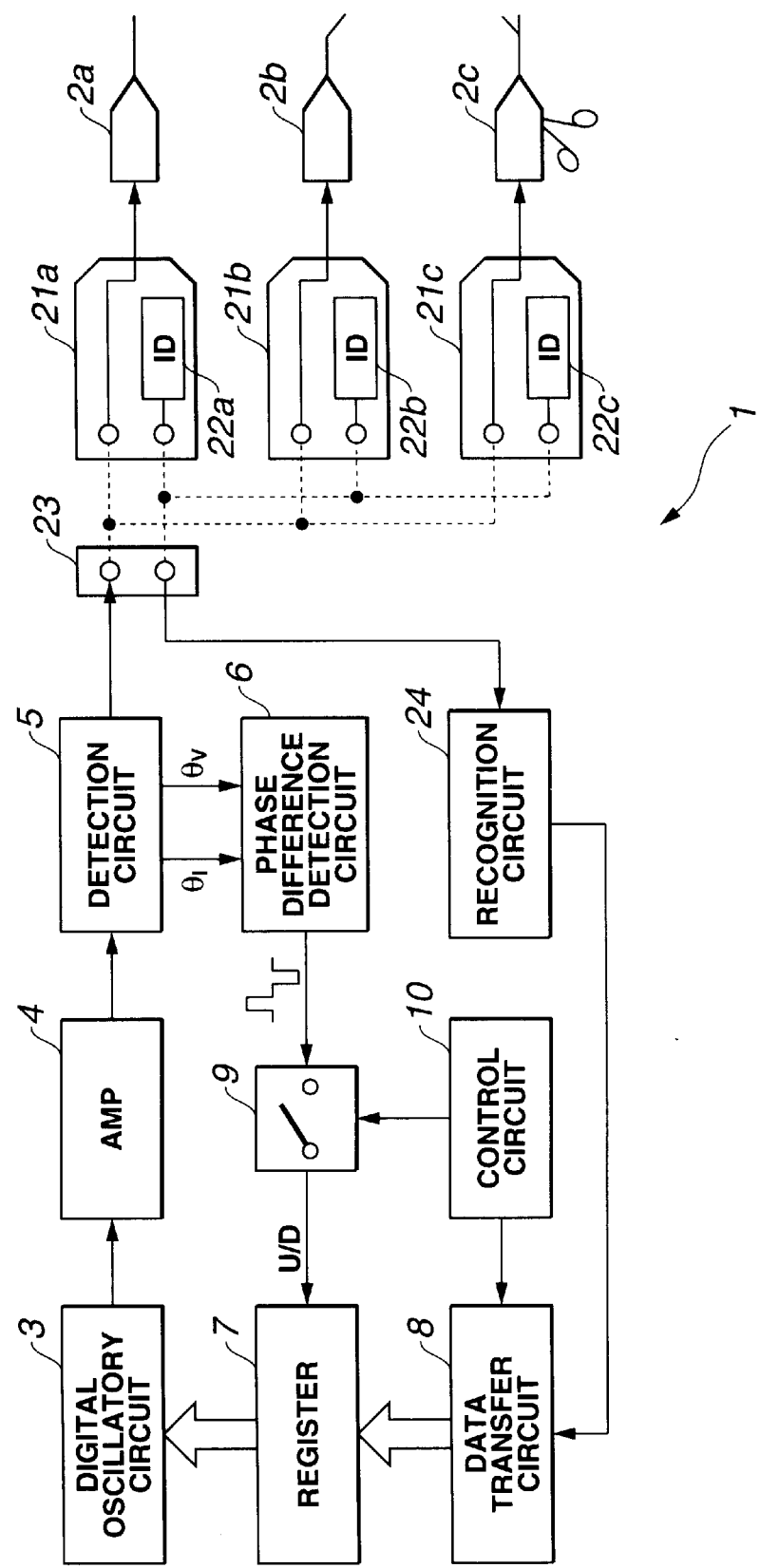
FIG. 3 is a block diagram showing the configuration of an ultrasonic driving apparatus in accordance with a second embodiment of the present invention.

Specifically, as shown in FIG. 3, the ultrasonic transducers 2a, 2b, and 2c have plugs 21a, 21b, and 21c through which the ultrasonic transducers are selectively connected to an ultrasonic driving apparatus 1. Identification (ID) devices 22a, 22b, and 22c with which the ultrasonic transducers are identified are incorporated in the plugs 21a, 21b, and 21c.

On the other hand, the ultrasonic driving apparatus 1 has a connector 23 to which the plugs 21a, 21b, and 21c can be inserted, and a recognition circuit 24 for recognizing the identification devices 22a, 22b, and 22c so as to discriminate the ultrasonic transducers 2a, 2b, and 2c. A data transfer circuit 8 transfers digital frequency data, which represents a selected one of the stored resonance frequencies fr of the ultrasonic transducers 2a, 2b, and 2c or frequencies close to the resonance frequencies, to a register 7.

(Operations)

In the present embodiment, when the ultrasonic driving apparatus is activated, a digital oscillatory circuit 3 is oscillated based on digital frequency data that represents the resonance frequency fr of a selected one of the ultrasonic transducers 2a, 2b, 2c or a frequency close to the resonance frequency.

Herein, the ultrasonic transducers 2a, 2b, and 2c can be adapted to a plurality of types of handpieces that are included in an ultrasonic operation system and designed for different purposes of use.

(Advantages)

As mentioned above, the present embodiment can provide the same advantages as the first embodiment can. In addition, when the resonance frequencies fr of the ultrasonic transducers 2a, 2b, and 2c are different from one another, digital frequency data concerning the ultrasonic transducers is held in advance in the data transfer circuit 8. The digital frequency data of a selected ultrasonic transducer is transmitted to the register 7 according to the result of recognition performed by the recognition circuit 24, whereby the driving apparatus 1 is activated. Consequently, the driving apparatus 1 can be reliably locked on to the resonance frequency of each ultrasonic transducer.

Third Embodiment:

A third embodiment is nearly identical to the second embodiment. A difference alone will be described below. The same reference numerals will be assigned to components identical to those of the second embodiment, and the description of the components will be omitted.

(Constituent Features)

In the third embodiment, frequency data that represents the resonance frequency fr of an employed one of ultrasonic transducers 2a, 2b, and 2c is acquired directly from the ultrasonic transducer.

Figure 4:
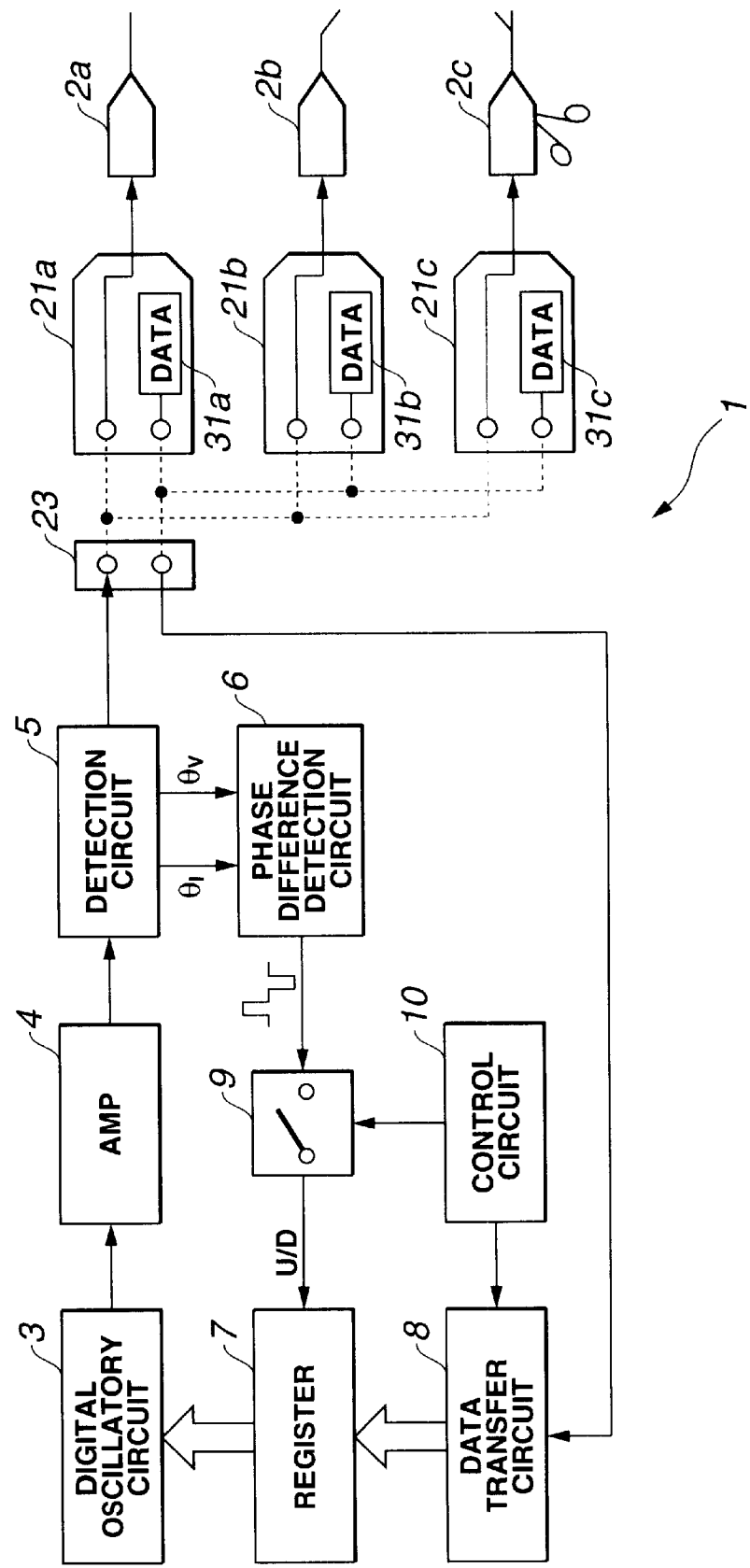
FIG. 4 is a block diagram showing the configuration of an ultrasonic driving apparatus in accordance with a third embodiment of the present invention.

Specifically, as shown in FIG. 4, data holding devices (DATA) 31a, 31b, and 31c that hold digital frequency data representing the resonance frequencies of the ultrasonic transducers are incorporated in plugs 21a, 21b, and 21c. The ultrasonic transducers 2a, 2b, and 2c are selectively connected to an ultrasonic driving apparatus 1 via the plugs 21a, 21b, and 21c. The ultrasonic driving apparatus 1 is configured so that a data transfer circuit 8 reads digital frequency data from the data holding device 31a, 31b, or 31c, and transfers the read data to a register 7.

(Operations)

The resonance frequencies fr of the ultrasonic transducers 2a, 2b, and 2c are different from one another. At this time, the ultrasonic transducers by themselves hold their digital frequency data. The digital frequency data of a selected ultrasonic transducer is held in the data transfer circuit 8, and then transferred to the register 7. The ultrasonic driving apparatus 1 is then activated.

(Advantages)

As mentioned above, the present embodiment can provide the same advantages as the second embodiment can.

Fourth Embodiment:

A fourth embodiment is nearly identical to the first embodiment. A difference alone will be described below. The same reference numerals will be assigned to components identical to those of the first embodiment, and the description of the components will be omitted.

(Constituent Features)

Figure 5:
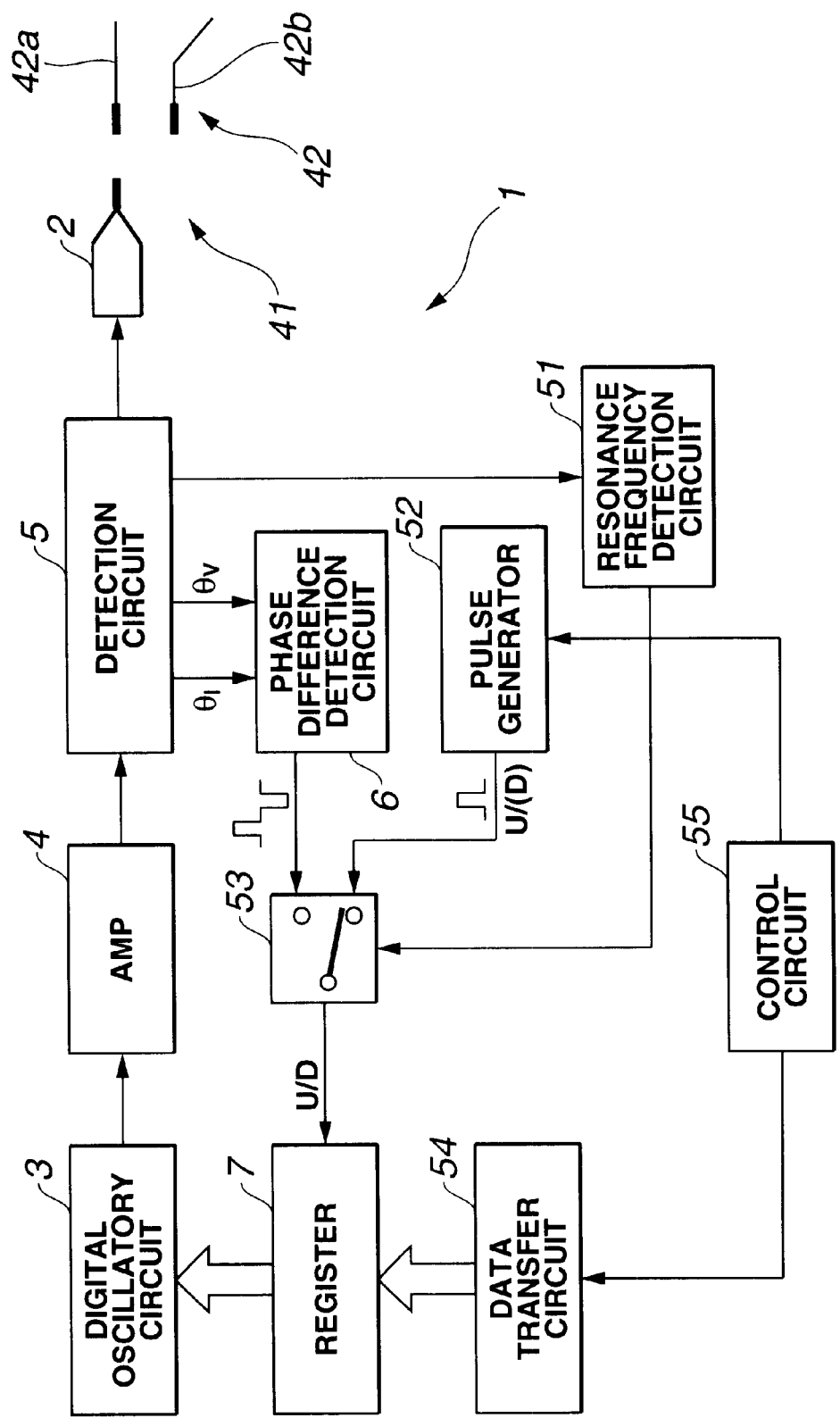
FIG. 5 to FIG. 7 are concerned with a fourth embodiment of the present invention.

In the fourth embodiment, as shown in FIG. 5, a handpiece 41 that is a therapeutic appliance included in an ultrasonic operation system and used to perform an operation consists of an ultrasonic transducer 2, and a probe 42 that is screwed to the ultrasonic transducer 2 for use. The probe 42 can be selected from among a plurality of types of probes. For example, a typical straight probe 42a and a curved probe 42b are available. A resonance frequency exhibited by the handpiece 41 varies depending on which of the probes 42 is screwed to the ultrasonic transducer 2.

An ultrasonic driving apparatus 1 of the present embodiment consists mainly of a resonance frequency detection circuit 51, a pulse generation circuit 52, a switch 53, a data transfer circuit 54, and a control circuit 55. The resonance frequency detection circuit 51 detects a resonance frequency exhibited by the handpiece 41. The pulse generation circuit 52 generates a signal which is transmitted to a register 7 and used to raise or lower at a certain proportion a frequency represented by digital frequency data held in the register 7.

The switch 53 selectively switches an output of a phase difference detection circuit 6 and an output of the pulse generation circuit 52 according to the result of detection performed by the resonance frequency detection circuit 51. The data transfer circuit 54 transfers frequency data, which represents a frequency higher or lower by a certain value than the resonance frequency of the handpiece 41, to the register 7. The control circuit 55 controls the actions of the pulse generation circuit 52 and data transfer circuit 54.

(Operations)

Figure 6:
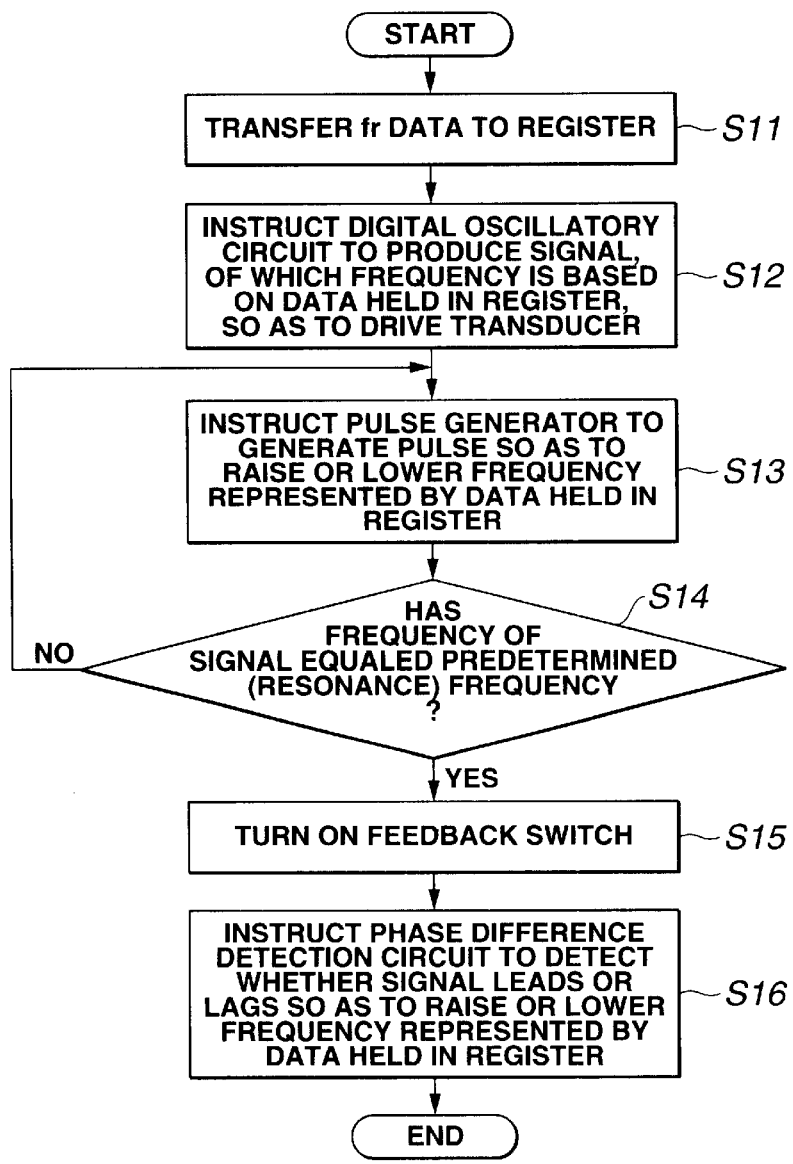

Referring to FIG. 6, actions performed in the present embodiment having the foregoing components will be described. For activating the ultrasonic driving apparatus 1, frequency data representing a frequency fr+Δf that is higher by a certain frequency Δf than a frequency fr close to the resonance frequency of the handpiece 41 is transferred from the data transfer circuit 54 to the register 7 at step S11. At step S12, the oscillatory circuit 3 produces a driving signal that has the same frequency as the one represented by the data read from the register 7. The driving signal is applied to the ultrasonic transducer 2 via an amplification circuit 4.

Figure 7:
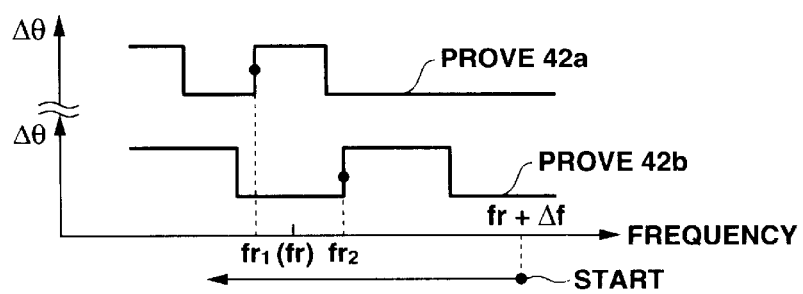

Herein, as shown in FIG. 7, when the probe 42a is screwed to the ultrasonic transducer 2, the handpiece shall exhibit a resonance frequency fr1. When the probe 42b is screwed to the ultrasonic transducer 2, the handpiece shall exhibit a resonance frequency fr2. Moreover, fr+Δf>f2>f1 shall be satisfied. A driving signal having a frequency read at a Start point in the graph of FIG. 7 is applied to the ultrasonic transducer 2.

In this state, the switch 53 selects the connection of the register 7 to an output terminal of the pulse generation circuit 52. A feedback sent from the detection circuit 5 is not fed to the register 7. Therefore, locking the ultrasonic driving apparatus 1 on to the resonance frequency using the feedback will not be carried out.

Referring back to FIG. 6, the pulse generation circuit 52 generates a pulsating signal at step S13. A frequency represented by digital frequency data held in the register 7 is lowered sequentially. For example, the frequency represented by the frequency data held in the register is lowered by 1 Hz synchronously with the leading edge of one pulse. If one hundred pulses are transmitted cyclically, the frequency represented by the frequency data held in the register is smoothly lowered by 1 kHz. The frequency at which the digital oscillatory circuit 3 is oscillated, that is, the frequency of a signal to be applied to the ultrasonic transducer 2 is swept at a certain change rate (see FIG. 7).

As mentioned above, a frequency-change signal whose frequency sequentially changes from a frequency higher than the resonance frequency of the ultrasonic transducer 2 towards the resonance frequency is applied to the ultrasonic transducer 2. Meanwhile, the resonance frequency detection circuit 51 monitors the frequency of the applied signal according to a detection signal output from the detection circuit 5 to see if the frequency of the applied signal is equal to the resonance frequency. If the frequency is not equal to the resonance frequency, the sweep action is continued. If it is detected that the frequency has become equal to the resonance frequency, the connections through the switch 53 are switched at step S15 so that an output of the phase difference detection circuit 6 will be fed to the register 7.

Consequently, at step S16, a control signal to be fed to the register 7 is changed to a signal output from the phase difference detection circuit 6. Thereafter, a control action is performed in order to lock the ultrasonic driving apparatus on to the resonance frequency. Specifically, the frequency represented by the frequency data stored in the register 7 is raised or lowered based on a feedback (U/D) from which a difference between the phase θv of an applied voltage and the phase θ of an induced current can be detected.

(Advantages)

As mentioned above, the present embodiment provides the same advantages as the first embodiment does. In addition, even when the probes to be screwed to the ultrasonic transducer 2 exhibit different resonance frequencies, when it is detected that the frequency of an applied signal has become equal to the resonance frequency of a probe employed, the connections through the switch 53 are switched. Since a feedback indicating a frequency band (from f1 to f2 shown in FIG. 11) within which the driving signal, oscillatory circuit, or driving apparatus can be locked on to the resonance frequency is detected, a PLL can be reliably set up in order to lock the driving signal on to the resonance frequency.

Fifth Embodiment:

A fifth embodiment is an ultrasonic operation system to which the components of an ultrasonic driving apparatus in accordance with any of the second to fourth embodiments are adapted. The fifth embodiment is nearly identical to the second embodiment and fourth embodiment. A difference alone will be described below. The same reference numerals will be assigned to components identical to those of the second and fourth embodiments, and the description of the components will be omitted.

(Constituent Features and Operations)

Figure 8:
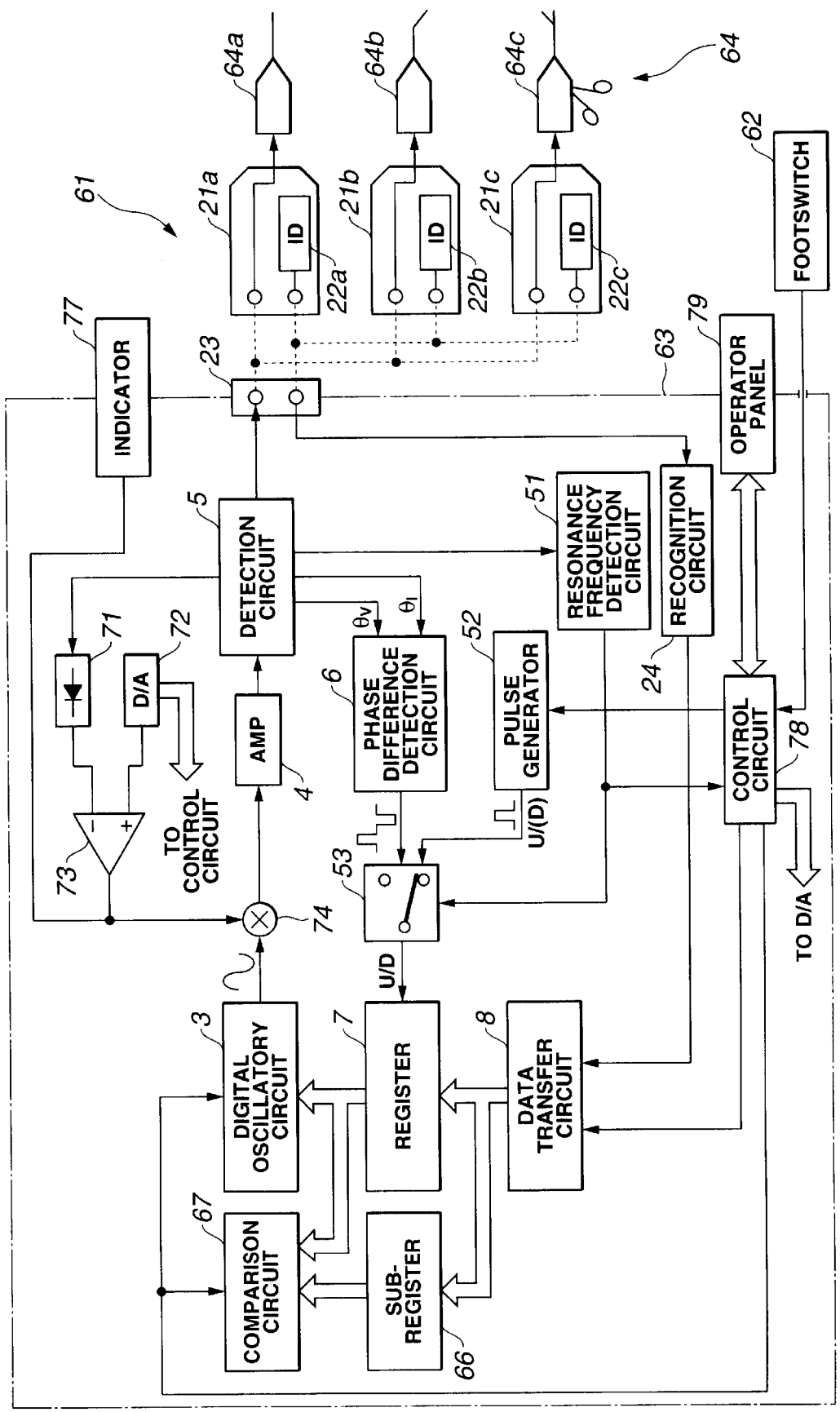
FIG. 8 is a block diagram showing the configuration of an ultrasonic operation system in accordance with a fifth embodiment of the present invention.

As shown in FIG. 8, an ultrasonic operation system 61 of the present embodiment consists mainly of a footswitch 62, a main apparatus 63, and a handpiece 64. The footswitch 62 is used to enable or disable output of ultrasonic energy. The main apparatus 63 includes an ultrasonic driving apparatus. The handpiece 64 includes a plurality of types of handpieces that exhibit different resonance frequencies and suit for different purposes of use.

The handpiece 64 includes handpieces 64a, 64b, and 64c that are intended for different purposes of use. A probe attached to the handpiece 64a can be replaced with a new one. A curved probe is attached to the handpiece 64b. A scissors-like probe is attached to the handpiece 64c. The handpiece 64 is provided with a plug 21 via which it is connected to the main apparatus 63. Identification devices (ID) 22a, 22b, and 22c (hereinafter generically 22) with which the handpieces are identified are incorporated in the plugs 21a, 21b, and 21c.

The main apparatus 63 includes a connector 23, a recognition circuit 24, a data transfer circuit 8, a sub-register 66, and a comparison circuit 67. The plug 22 of the handpiece 64 is inserted in the connector 23. The recognition circuit 24 recognizes the identification device 22 incorporated in the plug 21 and discriminates the handpiece 64 connected via the connector 23. The data transfer circuit 8 selects any of digital frequency data items, which are preserved in advance, according to the result of discrimination performed by the recognition circuit 24, and transfers the selected data to a register 7. The sub-register 66 receives the digital frequency data transferred from the data transfer circuit 8. The comparison circuit compares data held in the register 7 with data held in the sub-register 66. As described in relation to the second embodiment, the recognition circuit 24 discriminates the handpiece 64 connected to the main apparatus via the connector 23. Based on the result of discrimination, the data transfer circuit 8 transfers digital frequency data to the register 7. A driving signal whose frequency is equal to the frequency represented by the data is applied to an ultrasonic transducer incorporated in the handpiece 64.

At this time, the digital frequency data output from the data transfer circuit 8 represents, as described in relation to the fourth embodiment, a frequency fr+Δf higher by a certain frequency Δf than the resonance frequency fr of the handpiece 64.

Similarly to the fourth embodiment, even in the present embodiment, the digital frequency data held in the register 7 is sequentially modified responsively to output of a pulsating signal from a pulse generation circuit 52. A frequency at which a digital oscillatory circuit 3 is oscillated is changed. The frequency of a signal applied to the ultrasonic transducer in the handpiece 64 is swept. Meanwhile, a resonance frequency detection circuit 51 monitors the frequency of the applied signal to see if the frequency has become equal to the resonance frequency of the handpiece 64. When it is detected that the frequency of the applied signal has become equal to the resonance frequency, the connections through the switch 54 are switched. Consequently, a PLL is set up in order to lock a driving signal on to the resonance frequency using a feedback (U/D) output from a phase difference detection circuit 6.

The main apparatus 63 further includes a conversion circuit 71, a D/A conversion circuit 72, a differential amplification circuit 73, and a voltage-controlled amplification circuit 74. The conversion circuit 71 receives a signal, which represents the magnitude of a current flowing into the ultrasonic transducer in the handpiece 64, from the detection circuit 5, rectifies it, and converts it into a direct voltage. The D/A conversion circuit 72 converts a signal, with which the magnitude of a current flowing into the ultrasonic transducer in the handpiece 64 is determined and which is sent from a control circuit 78, into an analog form. The differential amplification circuit 73 compares a signal output from the conversion circuit 71 with a signal output from the D/A conversion circuit 72. The voltage-controlled amplification circuit 74 multiplies or amplifies a frequency-change signal output from the digital oscillatory circuit 3 in proportion to the magnitude of an output signal of the differential amplification circuit 73. These circuits constitute a constant-current control circuit 75 for stabilizing the value of a current that flows into the ultrasonic transducer in the handpiece 64.

Furthermore, the driving apparatus 63 includes the register 7 in which digital frequency data representing a frequency at which the digital oscillatory circuit 3 is oscillated is held, and a sub-register 66 in which frequency data received from the data transfer circuit 8 is held as it is. The digital frequency data held in the register 7 is modified time-sequentially because of phase locking performed after activation of the main apparatus. The comparison circuit 67 compares the digital frequency data held in the register 7 with initial digital frequency data held in the sub-register 66.

The main apparatus 63 is provided with an indicator 77 that is realized with an LED bar graph or the like. The bar graph indicates the magnitude of a voltage applied to the ultrasonic transducer or a current flowing thereinto, whereby the driven state of the ultrasonic transducer is indicated.

Incidentally, the control circuit 78 is a control circuit responsible for the whole of the main apparatus 63. The control circuit 78 transfers data to or from an operator panel 79, transmits data to the D/A conversion circuit 72, and determines the value of a current that flows into the ultrasonic transducer, that is, the amplitude of the current. Moreover, digital frequency data associated with each handpiece may be manually entered at the operator panel 79 in order to determine digital frequency data that is input as an initial value from the control circuit 78 to the data transfer circuit 8.

(Advantages)

As mentioned above, the present embodiment provides the same advantages as the second and fourth embodiments do. In addition, since the constant-current control circuit 75 stabilizes a current value, the ultrasonic transducer can be driven with the current of stable amplitude. This is attributable to the fact that the ultrasonic transducer generates oscillations whose amplitude is proportional to that of a current flowing into the ultrasonic transducer.

Moreover, the comparison circuit 76 compares time-sequentially varying digital frequency data held in the register 7 with initial digital frequency data held in the sub-register 66. Herein, the digital frequency data held in the register 7 represents a time-sequentially changing frequency. If a difference between the data items exceeds greatly a predetermined value, it is judged that any abnormality has occurred. The result of judgment may be transferred to the digital oscillatory circuit 3 in order to stop oscillations, or may be transmitted to the control circuit 78 in order to give a warning using the operator panel 79 or to halt all actions performed in the main apparatus. Depending on what action is performed, it is possible to detect an abnormal state, for example, to detect that the resonance frequency of the ultrasonic transducer or probe has varied greatly because of an abnormality, or that resonance is no longer attained because of a disconnection or a breakage.

Sixth Embodiment:

An ultrasonic operation system in accordance with the present embodiment consists mainly of, as shown in FIG. 9, an ultrasonic coagulation/incision apparatus 101 for outputting ultrasonic waves, a handpiece 102 used to treat a lesion, and a footswitch 103 used to control output of ultrasonic waves from the ultrasonic coagulation/incision apparatus 101.

As shown in FIG. 10, the handpiece 102 includes a transducer 104. The transducer 104 is driven via a sensing circuit 113 with a driving signal whose frequency is determined with an output of a digital PLL 111 incorporated in the ultrasonic coagulation/incision apparatus 101 and which is amplified by a power amplifier 112.

Moreover, the detection circuit 113 detects a voltage applied to the transducer 4 and an induced current, and produces phase signals (voltage phase signal and current phase signal) θv and θI.

The digital PLL 111 consists of a phase comparator 121, a frequency change setting circuit 122, an up/down counter 123, and a direct digital synthesizer (DDS) 124. The phase comparator 121 detects the sign (±) and magnitude of a phase difference between the phase signals θv and θI, and produces a phase different±signal.

The frequency change setting circuit 122 consists of a magnitude-of-phase difference sense unit 122*a*, first to third data storage units 122*b*, 122*c*, and 122*d*, and a change frequency arithmetic unit 122*e*. The magnitude-of-phase difference sense unit 122*a* is realized with a digital signal processor (DSP), inputs as an enabling signal a phase difference±signal output from the phase comparator 121, counts clock pulses, and thus senses the magnitude of the phase difference. The first to third data storage units 122*b*, 122*c*, and 122*d* hold three past outputs of the magnitude-of-phase difference sense unit 113*a*. The change frequency arithmetic unit 122*e* averages the values held in the first to third data storage units 122*b*, 122*c*, and 122*d* so as to calculate a change in a frequency at which the ultrasonic coagulation/incision apparatus is activated. The change frequency arithmetic unit 122*e* then produces a pulsating signal (up/down count signal) according to the result of calculation.

The up/down counter 123 detects the edge of an output (up/down count signal) of the frequency change setting circuit 22 using an initial-frequency signal sent from the CPU 125 as a reference. The up/down counter 123 then changes a driving frequency, at which the transducer is driven, by a predetermined frequency responsively to production one pulse of the up/down count signal. The up/down counter 123 thus produces a driving frequency setting signal.

Moreover, the DDS 124 produces a sine wave according to the driving frequency setting signal.

In the digital PLL 111, the frequency change setting circuit 122 produces an up/down count signal, with which the driving frequency setting signal is varied, using an output of the phase comparator 21 as a reference. The driving frequency corresponding to the frequency of a signal output from the DDS 124 via the up/down counter 123 is locked on to the resonance frequency of the transducer.

Moreover, a monitor circuit 126 monitors a driving-frequency signal, of which frequency corresponds to the driving frequency and which is applied to the transducer 104, to see if a phase difference between the applied signal and an initial-frequency signal falls within a predetermined range. If the difference exceeds the predetermined range, a non-phase-locked signal indicating that phase locking had failed is transmitted to the CPU 125.

FIG. 11A to FIG. 11C show actions performed in the frequency change setting circuit 122 included in the digital PLL 111 employed in the present embodiment.

The frequency change setting circuit 122 is, as mentioned above, realized with a DSP, and receives clock pulses, an initial-frequency signal sent from the CPU 25, and a phase difference±signal sent from the phase comparator 21.

The magnitude-of-phase difference sense unit 113*a* included in the frequency change setting circuit 122 receives a phase difference–(+) signal shown in FIG. 11B as an enabling signal, counts the clock pulses shown in FIG. 11A, and thus senses the magnitude of the phase difference–signal (the result of counting is shown as Cn in FIG. 11B).

Sensed data Cn is held in the first data storage unit 122*b*. Data items (Cn-1 and Cn-2) having been held in the first and second data storage units 122*b* and 122*c* so far are stocked in the second and third data storage units 122*c* and 122*d*.

The change frequency arithmetic unit 122*e* averages the results of sensing performed three times by the magnitude-of-phase difference sense unit, which are stocked, and produces a pulsating signal that has an average magnitude. The pulsating signal is provided as an output up (down) count signal.

Up (down) count signal=(Cn+Cn-1+Cn-2)/3 where Cn denotes the number of clock pulses counted during a period during which the phase difference±signal is low.

Responsively to production of one pulse of the up/down count signal, the up/down counter 123 changes the driving frequency setting signal by a predetermined frequency with an initial-frequency signal sent from the CPU 125 as a reference (FIG. 11C).

The DDS 124 changes the frequency of an output sine wave according to the driving frequency setting signal, whereby the output sine wave is locked on to the resonance frequency.

Through the above calculation, currently acquired data and past data are averaged. Therefore, even when impedance varies instantaneously, the driving frequency will not change so greatly that phase locking may fail.

Moreover, if the transducer 104 is broken or the like to offer high impedance all the time, phase locking will fail.

When the ultrasonic transducer is driven at a frequency close to the resonance frequency of the ultrasonic transducer, even if an impedance Z becomes high instantaneously, the frequency of a driving signal will not change instantaneously. If the ultrasonic transducer is broken or any other abnormality occurs, the abnormality is recognized and the ultrasonic coagulation/incision apparatus is halted.

Seventh Embodiment:

A seventh embodiment is nearly identical to the sixth embodiment. A difference alone will be described below. The same reference numerals will be assigned to components identical to those of the sixth embodiment, and the description of the components will be omitted.

Figure 12:
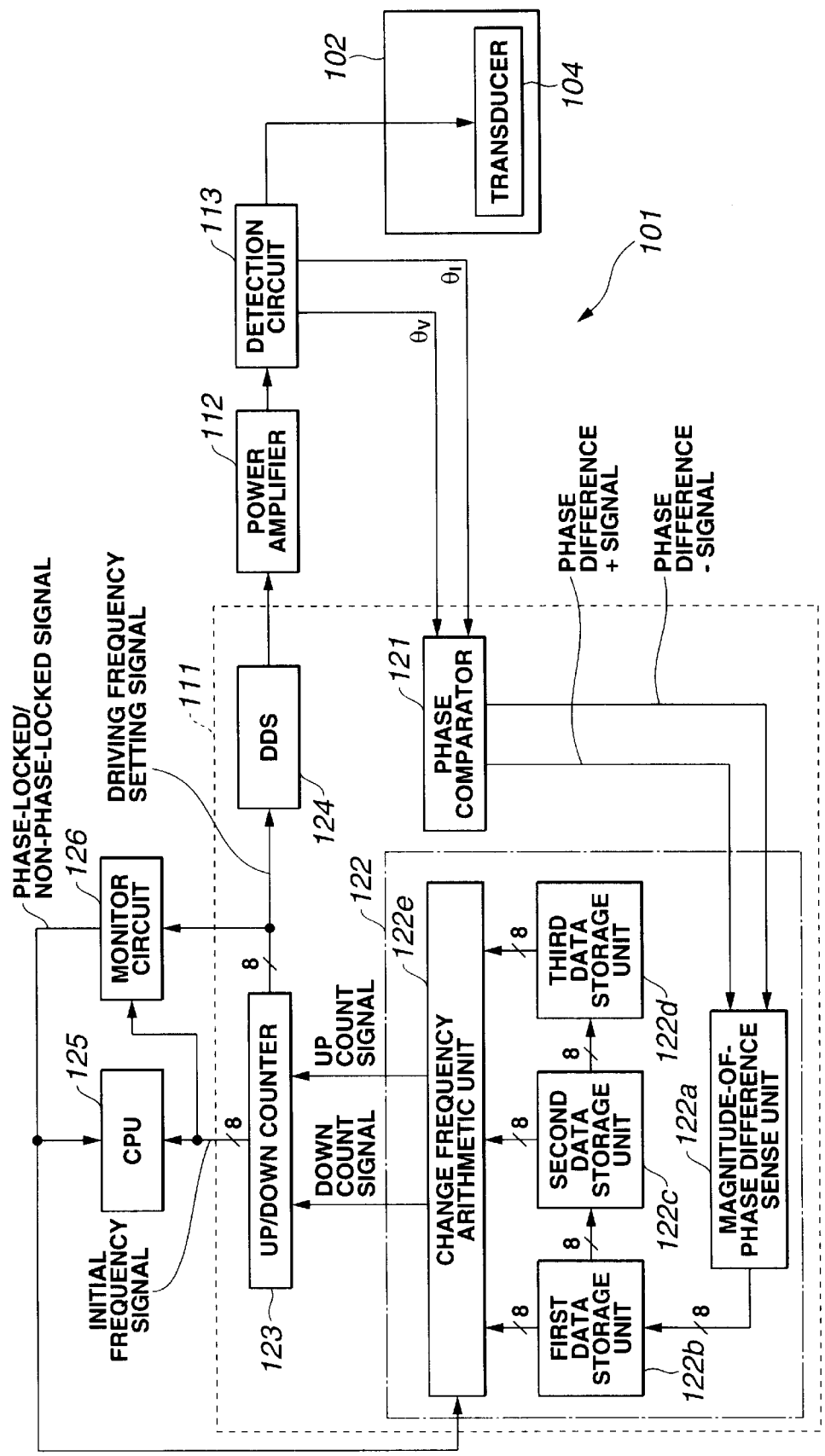
FIG. 12 is a block diagram showing the configuration of an ultrasonic coagulation/incision apparatus in accordance with a seventh embodiment of the present invention.

As shown in FIG. 12, in the seventh embodiment, a phase-locked/non-phase-locked signal that is an output of a monitor circuit 126 is one of inputs of a frequency change setting circuit 122.

The number of data items to be averaged by a change frequency arithmetic unit 122*e* is differentiated between when a driving signal is locked on to a resonance frequency (in a phase locking mode) and when the driving signal is not locked on to the resonance frequency (in a non-phase locking mode).

In the phase locking mode, the three data items (Cn, Cn-1, and Cn-2) held in first to third data storage units 122*b* to 122*d* are averaged in order to calculate a change frequency by which a driving frequency at which a transducer is driven is changed.

However, in the non-phase locking mode, the data Cn in the first data storage unit 122*b* is adopted as a change frequency by the frequency of a driving frequency setting signal is changed.

Consequently, in the phase locking mode, even if impedance becomes instantaneously high, phase locking is achieved stably. In the non-phase locking mode, a faster frequency change can be produced. This permits the CPU 125 to sense an abnormality quickly.

Eighth Embodiment:

An eighth embodiment is nearly identical to the sixth embodiment. A difference alone will be described below. The same reference numerals will be assigned to components identical to those of the sixth embodiment, and the description of the components will be omitted.

Figure 13:
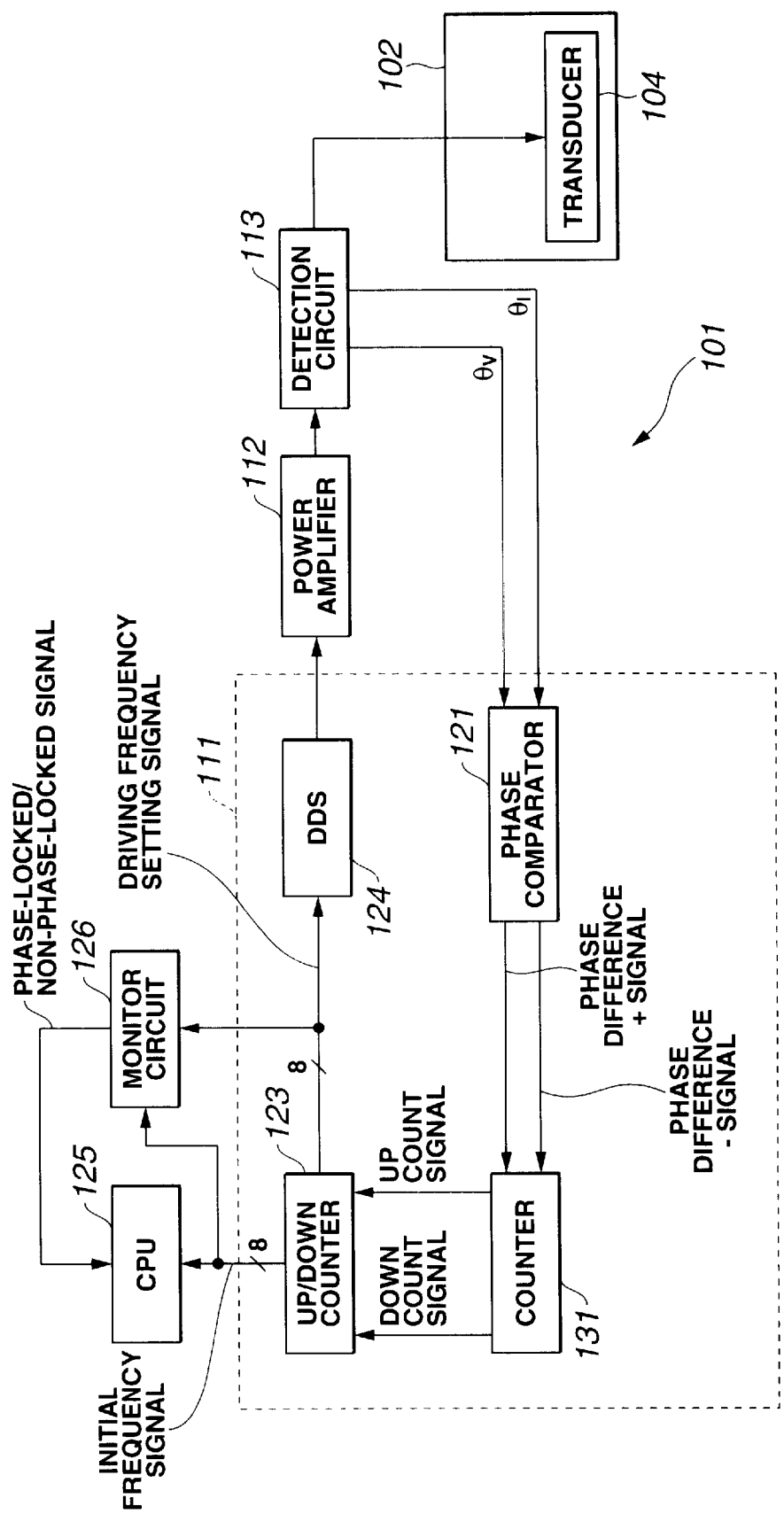
FIG. 13 is a block diagram showing the configuration of an ultrasonic coagulation/incision apparatus in accordance with an eighth embodiment of the present invention.

In the sixth and seventh embodiments, a phase difference±signal is adopted as an enabling signal, clock pulses are counted, and a DSP is used for calculation. The number of pulses of an up/down count signal that corresponds to the result of calculation is output to an up/down counter, whereby a driving signal is locked on to a resonance frequency of a transducer. In the present embodiment, as shown in FIG. 13, a counter 131 is substituted for a frequency change setting circuit 122. A fraction of the frequency of a phase difference±signal is calculated in order to produce an up/down count signal.

In the present embodiment, similarly to the sixth and seventh embodiments, the magnitude of the phase difference±signal is not reflected on the up/down count signal (whether a phase difference is large or not does not affect locking of a driving signal on to a resonance frequency). Since a fraction of the frequency of the phase difference±signal is calculated, the number of pulses of the up/down count signal to be produced relative to the number of pulses of the phase difference±signal can be decreased. Even when phase signals θv and θI contain a noise, changing a driving frequency at which a transducer is driven will not be affected terribly.

Moreover, the fraction of the frequency of the phase difference±signal may be changed from a quarter to a half or vice versa depending on whichever of phase locking and non-phase locking modes is set. In the phase locking mode, one pulse of the up/down count signal is produced relative to four pulses of the phase difference±signal. In the non-phase locking mode, one pulse of the up/down signal is produced relative to two pulses of the phase difference±signal.

An up/down counter 123 changes a driving frequency setting signal by 1 Hz responsively to production of one pulse of the up/down count signal. Consequently, the same advantages as those provided by the sixth and seventh embodiment can be exerted inexpensively.

Moreover, the responses of all the circuits incorporated in an ultrasonic coagulation/incision apparatus 1 may be delayed. This is helpful in preventing oscillations of all the circuits.

Figure 14:
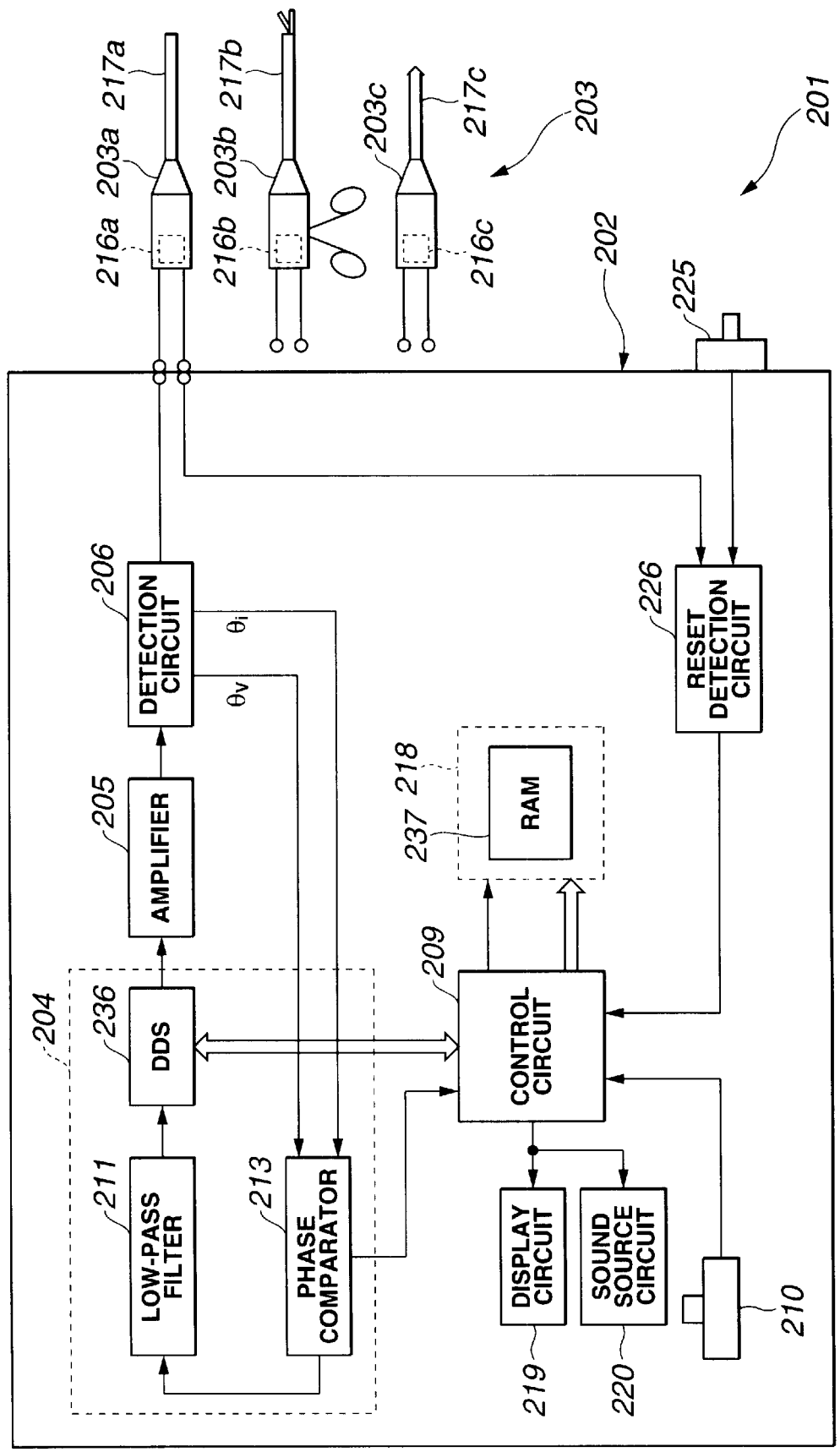
FIG. 14 shows the configuration of an ultrasonic operation system in accordance with a ninth embodiment of the present invention.

Ninth Embodiment:

As shown in FIG. 14, an ultrasonic operation system 201 of the present embodiment consists mainly of a main apparatus 202, and a handpiece 203 serving as an ultrasonic surgical appliance to be connected to the main apparatus 202 so that it can be freely disconnected therefrom. An ultrasonic transducer for converting ultrasonic energy supplied from the main apparatus 202 into ultrasonic mechanical oscillations is incorporated in the handpiece 203.

The handpiece 203 falls into handpieces 203A, 203B, and 203C of different shapes. Built-in ultrasonic transducers 216a, 216b, and 16c exhibit different resonance frequencies dependent on the shapes. Moreover, the resonance frequencies differ with the lengths or thicknesses of probes 217a, 217b, and 217c.

A drive circuit 204 included in the main apparatus 202 produces a signal with which ultrasonic energy is generated. An amplifier 520 is connected to the drive circuit 204. The amplifier 205 amplifies power of ultrasonic energy produced by the drive circuit 204. A detection circuit 206 is connected to the amplifier 205.

The detection circuit 206 detects a voltage phase signal θv and a current phase signal θi from the ultrasonic energy amplified by the amplifier 205. The detection circuit 206 also detects an impedance |Z| offered when the handpiece 203I (I denotes a, b, or c) is driven. The detected voltage phase signal θv is transferred to the drive circuit 204.

Moreover, the detection circuit 206 is connected to the handpiece 203I and supplies ultrasonic energy to the handpiece 203I.

The drive circuit 204 consists of a phase comparator 213, a low-pass filter 211, and a direct digital synthesizer (DDS) 236. The phase comparator 213 compares phases. The low-pass filter 211 passes a low-frequency component of an output signal of the phase comparator 213. The DDS 236 is a variable oscillator that is oscillated at a frequency variable with digital data. The digital data represents the voltage of the low-frequency signal component having passed through the low-pass filter 211.

A voltage phase signal θv detected by the detection circuit 206 is applied to one terminal of the phase comparator 213. A current phase signal θi is applied to the other terminal thereof. The phase comparator 213 outputs a signal that corrects the frequency of a driving signal so that both the phase signals will be in phase with each other.

The low-pass filter 211 is connected to the phase comparator 213. A signal output from the phase comparator 213 is filtered in order to pass a low-frequency component, whereby a voltage needed to match the phase of an applied voltage with the phase of an induced current is produced. The DDS 236 is connected to the low-pass filter 211. Using the voltage produced by the low-pass filter 211, the DDS 236 provides an oscillatory output, at the frequency of which a voltage should be applied so that the voltage will be in phase with an induced current, to the amplifier 5. Thus, a PLL is realized.

Moreover, a control circuit 209 is connected to a random access memory (RAM) 237 serving as a frequency preserving means 218 in which a frequency is preserved, and a display circuit 219 and a sound source circuit 220 which serve as a notifying means. The control circuit 209 is connected to an output switch 210. The output switch 210 transfers an on/off signal, with which the handpiece 203I is driven, to the control circuit 9.

In the ultrasonic operation system 201, an oscillatory output of the DDS 236 is fed to the amplifier 205, and an oscillation control terminal of the DDS 236 is connected to the control circuit 209.

Moreover, the main apparatus 202 is provided with a reset switch 225 that is used to issue a reset instruction. An output signal of the reset switch 225 is fed to a reset detection circuit 226 that detects a reset instruction. The reset detection circuit 226 detects an input signal received from the reset switch 225, and communicates the result of detection to the control circuit 209.

Next, operations to be exerted by the present embodiment will be described below.

First, before an output on signal of the output switch 210 is transferred, the control circuit 209 transmits digital data to the DDS 232 that serves as a variable oscillator. Based on the digital data, the handpiece 203 should be driven by sweeping the frequency of an oscillatory output from a high frequency close to a resonance frequency from a low frequency close thereto or vice versa.

The voltage phase signal θv and current phase signal θi detected by the detection circuit 206 are transferred to the phase comparator 213. It is detected whether the phase signals have the same relationship as they have when they are detected from an oscillatory output whose frequency corresponds to a resonance frequency. In other words, when it is detected that the voltage phase signal θv and current phase signal θi become in phase with each other, a signal is transferred to the control circuit 209.

The control circuit 209 sweeps the frequency of an oscillatory output. When the signal causing the phase signals to become in phase with each other is transferred from the phase comparator 213, frequency digital data with which the control circuit 209 controls the DDS 236 is transferred and preserved in the RAM 237 serving as the frequency preserving means 218.

For actually providing an oscillatory output, the frequency data preserved in the RAM 237 is used to start oscillating the DDS 236. Thus, a PLL is set up. For performing an ultrasonic operation, the output switch 210 may be turned on or off frequently. When an operator turns on the output switch 210, except when the operator turns on the output switch 210 for the first time, the operator need not wait but can soon drive the handpiece 203I at the resonance frequency of the handpiece 203I. Thus, the ultrasonic operation system having an excellent response characteristic and being user-friendly can be provided.

When the output switch 210 is turned on or off repeatedly, a total time during which the output switch 210 is held on may be long. In this case, the ultrasonic transducer 216i may dissipate heat and the resonance frequency of the ultrasonic transducer 216i may change gradually. However, frequency information acquired immediately before the output switch 210 is turned off last is preserved. Therefore, when the output switch is turned on next, the ultrasonic transducer is driven based on the preserved frequency information (except when a time interval from when the output switch is turned off to when it is turned on is large). Consequently, a change in the resonance frequency is so small that a PLL can be set up shortly.

According to the present embodiment, frequency information acquired while the ultrasonic operation system is in use is acquired nearly in real time. When the output switch is turned off and then on, frequency information acquired when the output switch is turned off immediately before it is turned on is used for oscillation. Even when the use time of the handpiece 203I is short or so long as to raise the temperature of the handpiece, the handpiece can be shortly driven in practice. This leads to improved maneuverability (user-friendliness).

Moreover, when a reset signal is fed to the control circuit 209, the frequency of an oscillatory output may be swept without use of resonance frequency data stored in the RAM 237.

Advantages provided by the present embodiment will be described. That is to say, frequency data that is digital data is transferred to or from the DDS 236 that is a variable oscillator, the RAM 237 that is a frequency preserving means, and the control circuit 209. A difference in performance of each circuit element from product to product is small, and each circuit element exhibits an excellent temperature characteristic. Moreover, a CPU may be included for arithmetic operations, and a control action can be readily improved by upgrading software. Thus, excellent expandability can be provided.

According to the aforesaid description, information of a frequency control voltage stored last in the frequency preserving means 218 is employed when the output switch 210 is turned on again. Alternatively, a time during which the output switch 210 is held on or a time interval from when the output switch 210 is turned on to when it is turned on next may be measured. By judging the length of the time or detecting the temperature of the ultrasonic transducer 216i incorporated in the ultrasonic probe 203I, the frequency control voltage may be varied or changed to another.

Specifically, when the output switch 210 is held on for a long period of time, the ultrasonic transducer 216i may dissipate heat and the resonance frequency of the ultrasonic transducer 216i may differ from a resonance frequency thereof exhibited when the ultrasonic transducer 216 dissipates no heat.

In this case, when the output switch 210 is turned on again, if the temperature of the ultrasonic transducer 216i has not changed very much, the resonance frequency of the ultrasonic transducer will hardly differ from a frequency specified in the information of the frequency control voltage stored last in the frequency preserving means 218. Therefore, a PLL can be set up shortly.

However, when a long time has elapsed until the output switch 210 is turned on again, heat dissipation has been suppressed. In this case, information of a frequency control voltage stored first in the frequency preserving means 218 when the output switch 210 is turned on first in order to set up a PLL may be rather adopted.

When a long time has elapsed until the output switch 210 is turned on next, information of a frequency control voltage stored first in the frequency preserving means 218 may be adopted. When a not so long time has elapsed until the output switch 210 is turned on next, information of a frequency control voltage stored last in the frequency preserving means 218 may be adopted (selected). Instead of measuring the time, frequency control voltages may be switched depending on the temperature of the ultrasonic transducer.

Figure 15:
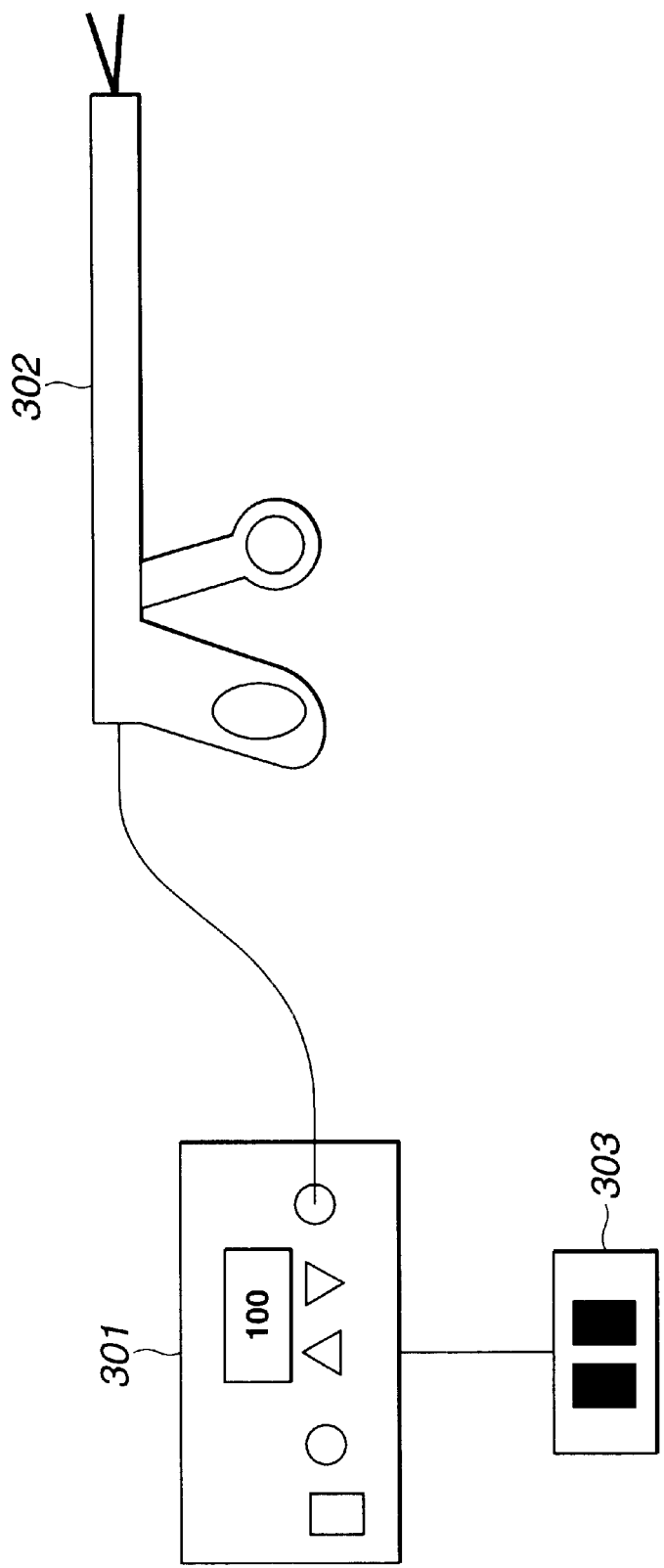
FIG. 15 to FIG. 18 are concerned with a tenth embodiment of the present invention.

Tenth Embodiment:

An ultrasonic operation system of the present embodiment consists mainly of, as shown in FIG. 15, an ultrasonic coagulation/incision apparatus 301 for outputting ultrasonic waves, a handpiece 302 used for treatment, and a footswitch 303 used to control output of ultrasonic waves from the ultrasonic coagulation/incision apparatus 301.

Figure 16:
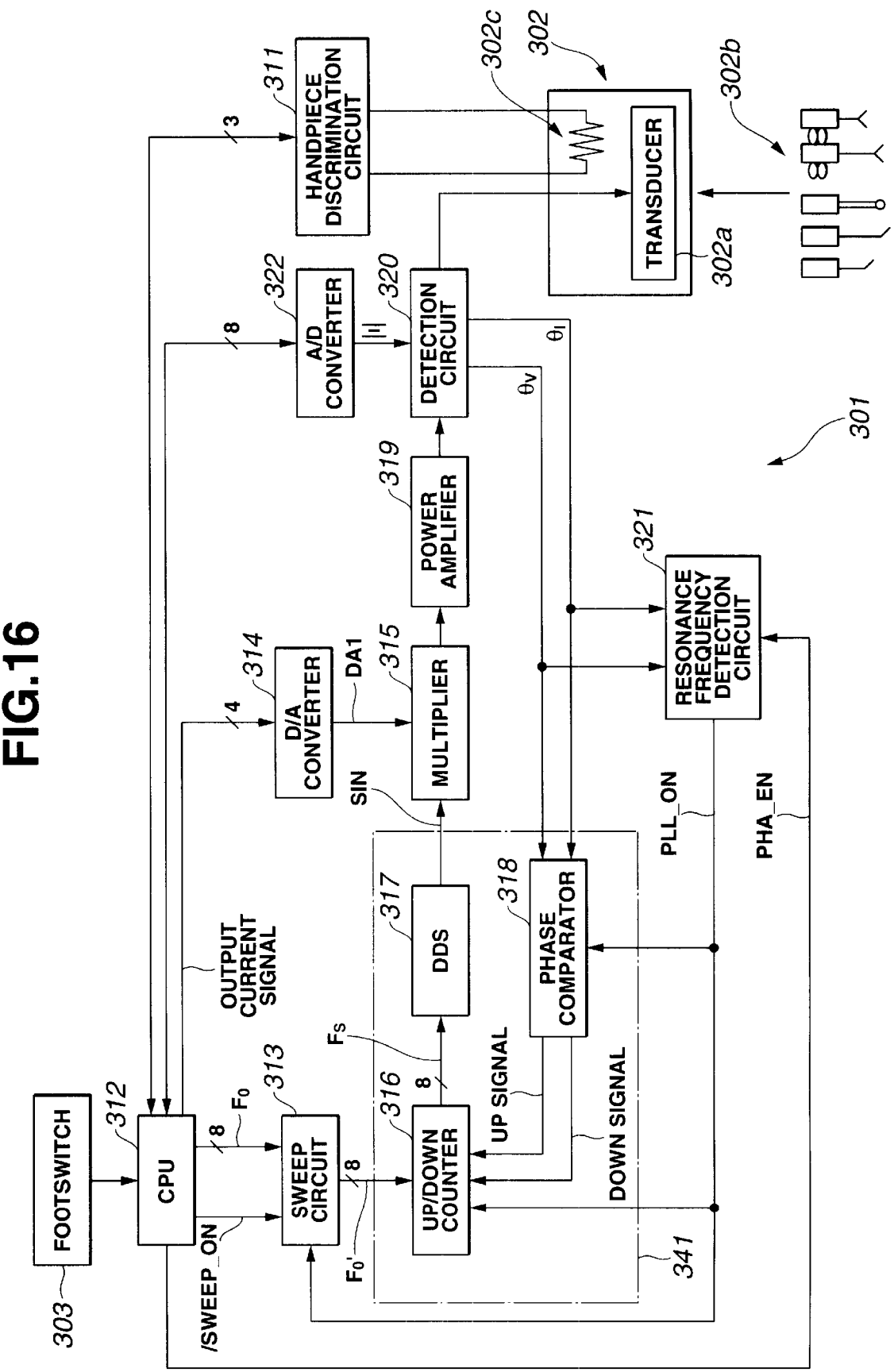

The handpiece 302 includes, as shown in FIG. 16, a transducer 302a and is integrated with various types of probes 302b. The handpiece 302 is attachable or detachable to or from the ultrasonic coagulation/incision apparatus 301. An electric signal applied from the ultrasonic coagulation/incision apparatus 301 is converted into mechanical oscillations by the transducer 302a. Mechanical oscillations made by the probe 302 connected to the transducer 302a are used for treatment.

A discrimination resistor 302c used to discriminate the type of handpiece 302 is included in the handpiece 302. A constant to which the discrimination resistor 302c is set varies depending on the type of handpiece 302. A handpiece (HP) discrimination circuit 311 detects a resistance exhibited by the discrimination resistor 2c, and transmits the result of discrimination (type of handpiece) to a CPU 312. The CPU 312 judges from the result of discrimination what type of handpiece is connected.

In the ultrasonic coagulation/incision apparatus 301, as shown in FIG. 16, when an operator turns on the footswitch 303, the CPU 312 sets a 8-bit initial frequency signal Fo according to the result of discrimination of the type of handpiece 302. After the initial frequency signal Fo is sent to a sweep circuit 313, a sweep start signal (/SWEEP_ON) is transmitted. Sweeping the frequency of a current output from the ultrasonic coagulation/incision apparatus is started in order to detect whether the frequency of the output current has become equal to a frequency Fr0. The frequency of the initial frequency signal Fo is a frequency adopted as an initial value at the start of sweeping the frequency of an output current.

Moreover, when it is detected whether the frequency of an output signal has become equal to the frequency Fr0, the CPU 312 outputs an initial output current signal of four bits long (30% of a maximum output current signal) to a D/A converter 314. The D/A converter 314 converts the signal into an analog form and outputs the resultant signal to a multiplier 315.

The sweep circuit 313 counts down pulses of the initial frequency signal FO at regular intervals, and produces a sweep signal Fo'. When the frequency of an output current becomes equal to the frequency Fr0, the initial frequency signal F0 is passed through an up/down counter 316, and fed as a driving frequency setting signal Fs to a DDS 317.

The up/down counter 316 and a phase comparator 18 are activated in order to realize a PLL for phase locking, and therefore used to lock the frequency of an output current on to a resonance frequency. The up/down counter 316 and phase comparator 318 are therefore designed to operate only while an input signal PLL_ON is on. Incidentally, the input signal PLL_ON is turned on after the frequency of an output current becomes equal to the frequency Fr0.

The DDS 317 outputs a sine wave whose frequency corresponds to that of the driving frequency setting signal Fs. The sine wave output from the DDS 317 is fed to the multiplier 315, and multiplied by a signal DA1 which the D/A converter 314 produces by converting an output current signal sent from the CPU 312 into an analog form.

A resultant sine wave output from the multiplier 315 is amplified by a power amplifier 319, and applied to the transducer 302a in the handpiece 302 via a detection circuit 320.

The detection circuit 320 detects a (voltage) phase signal θv and a (current) phase signal θI from ultrasonic waves of an applied voltage and an induced current. The detection circuit 320 also detects a root-mean-square value |I| of the induced current. The (voltage) phase signal θv and (current) phase signal θI are fed to a resonance frequency detection circuit 321. The root-mean-square value |I| of the induced current is converted into an 8-bit digital signal by an A/D converter 322 and sent to the CPU 312.

The CPU 312 changes a reference value |I|ref according to the result of discrimination of the type of handpiece 302. For example, when a probe that is so long as to incur a large load is incorporated in the handpiece, the reference value |I|ref is set to a small value. When a probe that is so short as to incur a not so large load is incorporated therein, the reference value |I|ref is set to a large value.

When the frequency of an output current is swept to become equal to the frequency Fr0, the CPU 312 compares the root-mean-square value |I| with the reference value |I|ref. When the root-mean-square value |I| becomes larger than the reference value |I|ref, the CPU 312 drive a signal /PHA_EN to an on voltage level and transmits the resultant signal /PHA_EN to the resonance frequency detection circuit 321.

Figure 17:
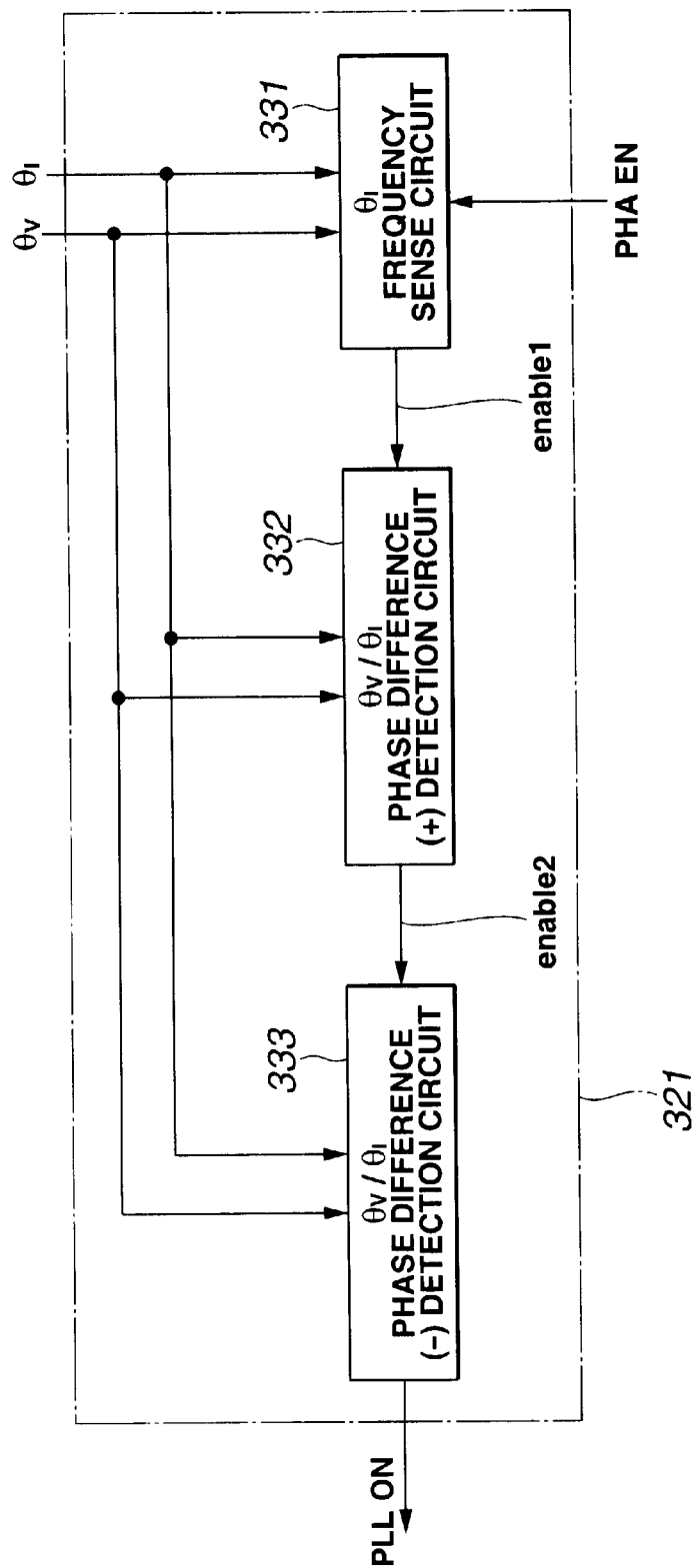

The resonance frequency detection circuit 321 consists of, as shown in FIG. 17, a θI frequency sensing circuit 311, a θI/θv phase difference (+) detection circuit 332, and a θI/θv phase difference (−) detection circuit 333.

When the signal /PHA_EN is driven to the on level, the θI frequency sensing circuit 311 starts sensing. The θI frequency sensing circuit 311 is included on the assumption that the transducer 302a may be broken, a probe connected to the transducer may be broken, a duty factor of an output current may not reach 50%, or the output current may distort. The θI frequency sensing circuit 331 senses whether the frequency of the phase signal θI falls within ±10% of the frequency of the phase signal θv. After the sensing is completed, an enabling signal enable1 is driven to an on voltage level and sent to the θI/θv phase difference (+) detection circuit 332.

When the enabling signal enable1 is driven to the on level, the θI/θv phase difference (+) detection circuit 332 starts sensing. When the phase difference between the phase signals θI and θv makes a positive-to-negative transition, the θI/θv phase difference (+) detection circuit 332 senses in cooperation with the θI/θv phase difference (−) detection circuit 333, which will be described later, that the frequency of an output current has become equal to the frequency Fr0. This is because the frequency of an output current becomes equal to the frequency Fr0 at the positive-to-negative transition of the phase difference.

The θI/θv phase difference (+) detection circuit 332 senses whether the frequency of an output current to be swept falls within a frequency band ranging from the frequency Fr0 to a frequency F2 (a frequency band within which the phase difference is positive). In other words, the θI/θv phase difference (+) detection circuit 332 senses whether the phase difference of the induced current from the applied voltage remains positive for a certain time interval.

When it is sensed that the frequency of an output current to be swept falls within the frequency band within which the phase difference is positive, an enabling signal enable2 is driven to an on voltage level. The signal enable2 is then sent to the θI/θv phase difference (−) detection circuit 333.

When the enabling signal enable2 is driven to the on level, the θI/θv phase difference (−) detection circuit 333 starts sensing. For sensing whether the frequency of an output current becomes equal to the frequency Fr0 as mentioned above, the θI/θv phase difference (−) detection circuit 333 senses whether the frequency of an output current to be swept falls within a frequency band ranging from a frequency F1 to the frequency Fr0 (a frequency band within which the phase difference is negative). In other words, the θI/θv phase difference (−) detection circuit 333 senses whether the phase difference of the induced current from the applied voltage remains negative for a certain time interval.

When it is sensed that the frequency of an output current to be swept falls within the frequency band in which the phase difference is negative, it means that the phase difference has made a positive-to-negative transition, that is, the frequency of an output current has become equal to the frequency Fr0. Therefore, for setting up a PLL, the θI/θv phase difference (−) detection circuit 333 drives a signal PLL ON to an on voltage level.

When the signal PLL_ON is driven to the on level, the sweep circuit 313 stops sweeping the frequency of an output current. Since it is sensed that the frequency of an output current has become equal to the frequency Fr0 that is the resonance frequency, the frequency of an output current will not be changed any longer.

When the signal PLL_ON is driven to the on level, the up/down counter 316 and phase comparator 318 are started to operate. A PLL 341 is set up to lock the frequency of an output current on to the resonance frequency.

The phase comparator 318 detects a phase difference between the voltage phase signal θv and current phase signal θI, and outputs a control signal (hereinafter an up/down signal) with which the frequency of a current (sine wave) output from the DDS 317 is raised or lowered so that the output current will be locked on to the resonance frequency. The control signal is then fed to the up/down counter 316.

Based on the frequency Fr0 detected when it is sensed whether the frequency of an output current has become equal to a resonance frequency and the up/down signal sent from the phase comparator 318, the up/down counter 316 outputs a driving frequency setting signal Fs. The driving frequency setting signal Fs is a setting signal to the frequency of which the frequency of a current actually output from the DDS 317 is set.

Moreover, assuming that the handpiece 302 incurs a large load, if the frequency of an output current equals the frequency Fr0, high impedance may be offered. In this case, the maximum root-mean-square value |I| becomes smaller than the reference value |I|ref. Consequently, it may be a failure to detect whether the frequency of an output current has become equal to the frequency Fr0.

When the frequency of an output current is swept for the first time, if it is a failure to detect whether the frequency of an output current has become equal to the frequency Fr0, a set value of the output current whose frequency is checked to see if the frequency has become equal to the frequency Fr0 is raised in units of 10% (up to, for example, 70%).

Specifically, the CPU 312 transmits a 4-bit output current setting signal to the D/A conversion circuit 315. The D/A conversion circuit 315 converts the signal into an analog form and outputs the resultant signal to the multiplier 308.

When an output current is large, if the frequency of the output current equals the frequency Fr0, impedance to be offered is lower. Therefore, it can be readily detected whether the frequency of the output current has become equal to the frequency Fr0.

Next, a flow of processing performed in the ultrasonic coagulation/incision apparatus 301 having the aforesaid components until a PLL is set up will be described below.

Figure 18:
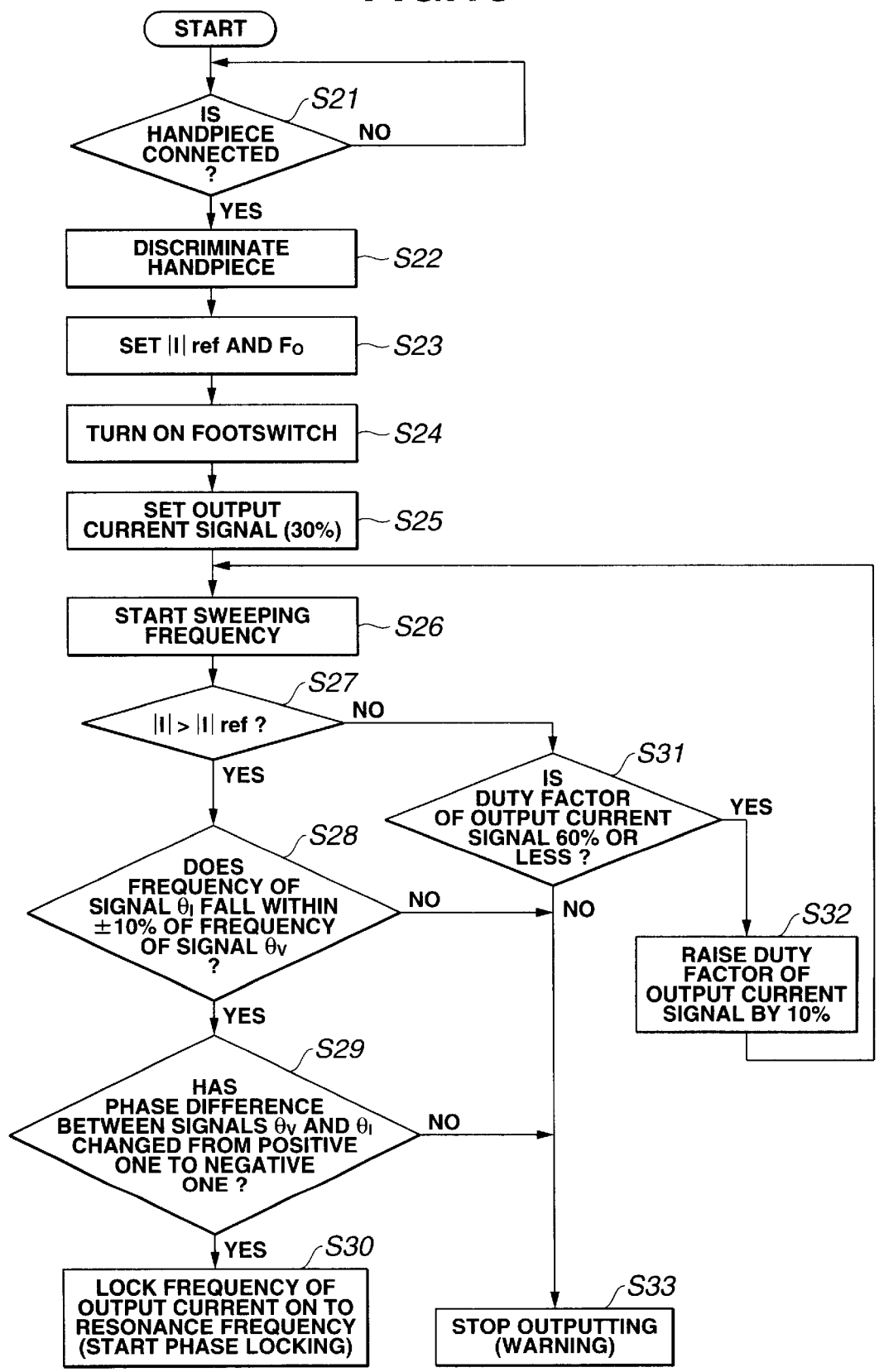

As described in FIG. 18, the handpiece 302 is connected to the ultrasonic coagulation/incision apparatus at step S21. The type of connected handpiece 302 is judged at step S22. The initial-frequency signal Fo and reference value |I|ref are set depending on the type of handpiece 302 at step S23.

At step S24, an operator turns on the footswitch 303. At step S25, the CPU 312 outputs a 4-bit output current signal to the D/A converter 314 to set the value of an output current so that it can be detected whether the frequency of the output current has become equal to the frequency Fr0. The D/A converter 314 converts the signal into an analog form and outputs the resultant signal to the multiplier 315.

At step S25, the CPU 312 transmits an 8-bit initial-frequency signal Fo to the sweep circuit 313. Thereafter, a sweep start signal /SWEEP_ON is transmitted, and the sweep circuit 13 starts sweeping the frequency of the output current so as to make the frequency equal to the frequency Fr0.

At step S26, the number of times by which the sweeping is performed is counted. At step S27, the CPU 312 judges whether the root-mean-square value |I| of the output current has exceeded the reference value |I|ref. If the root-mean-square value |I| of the output current has exceeded the reference value |I|ref, the resonance frequency detection circuit 21 judges at step S28 whether the frequency of a phase signal θI falls within ±10% of the frequency of a phase signal θv. If the frequency of a phase signal θI falls within ±10% of the frequency of a phase signal θv, control is passed to step S29.

At step S29, the resonance frequency detection circuit 321 judges whether the phase difference between the voltage phase signal θv and current phase signal θI has made a positive-to-negative transition. If the phase difference between the voltage phase signal θv and current phase signal θI has made a positive-to-negative transition, it signifies that the frequency of the output current has become equal to the frequency Fr0. Therefore, sweeping the frequency of the output current is stopped at step S30. The up/down counter 316 and phase comparator 318 are activated, whereby the PLL 341 is set up in order to lock the frequency of an actual output current on to the resonance frequency.

If it is judged at step S27 that the root-mean-square value |I| of the output current has not exceeded the reference value |I|ref, it is judged at step S31 whether the duty factor of the output current signal is 60% or less. If the duty factor of the output current signal is 60% or less, the CPU 312 raises the output current signal by 10% at step S32. Control is then returned to step S5, and the processing is terminated.

If it is judged at step S28 that the frequency of a phase signal θI does not fall within ±10% of the frequency of a phase signal θv, if it is judged at step S29 that the phase difference between the voltage phase signal θv and current phase signal θI has not made a positive-to-negative transition, or if it is judged at step S31 that the duty factor of the output current signal has exceeded 60%, a warning is given at step S33. Outputting is then stopped.

As mentioned above, according to the present embodiment, the CPU 312 changes the reference value |I|ref depending on the type of handpiece 302. Even when various types of handpieces 2 are employed or a large load is imposed on the handpiece 302, it can be sensed if the frequency of an output current has become equal to the frequency Fr0. Even when various types of handpieces are connected or a large load is imposed on a probe screwed to a transducer, it can be reliably detected whether the frequency of an output has become equal to the initial resonance frequency or the frequency Fr0.

Moreover, by sensing the positive-to-negative transition of the phase difference, it is detected whether the frequency of an output current has become equal to the frequency Fr0. Consequently, even if the phase signals θv and θI are affected by a noise, incorrect sensing will not take place.

For sweeping the frequency of an output current for the first time, the same processing as that described in FIG. 18 is carried out. During the first sweeping, a maximum root-mean-square value |I|max is detected. If the maximum value is smaller than an input current value |I|per permissible by the transducer 302a, the set value of an output current will not be raised in units of 10%. Instead, the CPU 312 may calculate an output current value, that does not exceed the input current value |I|per, using the ratio of the input current value |I|per to the maximum root-mean-square value |I|max. Thus, the output current value may be determined. In the case of the processing flow described in FIG. 18, if it is failed to sense whether the frequency of an output current has become equal to the frequency Fr0, the set value of an output current is raised gradually. When the frequency of an output current is swept for the second time, if a maximum possible current is supplied to the transducer 302a, the possibility of sensing whether the frequency of an output current has become equal to the frequency Fr0 can be improved.

Moreover, the reference value |I|ref with which an output current |I| is compared may be determined as mentioned below.

Specifically, when the frequency of an output current is swept, the output current |I| is monitored in order to detect a minimum value |I|min of the output current |I|. An offset current value |I|offset is added to the minimum value |I|min, and the sum is adopted as the reference value |I|ref.

Assuming that the reference value |I|ref is determined as mentioned above, the output current assumes the minimum value |I|min when it has a frequency F2. When the frequency of the output current falls within a frequency band higher than the frequency F2, a signal /PHA_EN is not driven to an on voltage level. Therefore, the frequency of the output current must be within a frequency band lower than the frequency F2. At this time, it can be sensed whether the phase difference has made a positive-to-negative transition.

Figure 19:
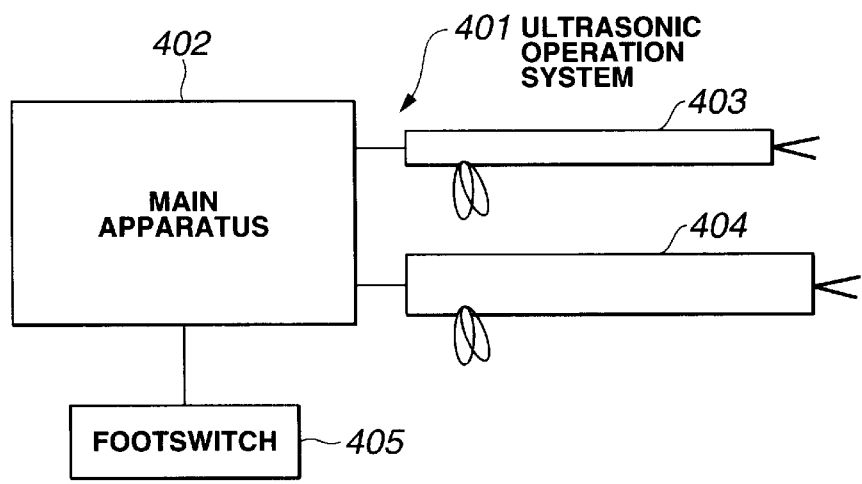
FIG. 19 to FIG. 21 are concerned with an eleventh embodiment of the present invention.

Eleventh Embodiment:

As shown in FIG. 19, an ultrasonic operation system 401 of the present embodiment consists mainly of a main apparatus 402, two types of handpieces 403 and 404 used to treat a living tissue with ultrasonic oscillations, and a footswitch 405. The main apparatus 402 included in the ultrasonic operation system 401 outputs high-frequency power to the handpiece 403 or 404. The outputting is controlled, that is, enabled or disabled using an output pedal of the footswitch 405.

The handpieces 403 and 404 are typical therapeutic appliances for the ultrasonic operation system 401. For example, the handpiece 403 exhibits a resonance frequency of 47 kHz that is a relatively high frequency, and can be shaped thinly. The handpiece 404 exhibits a resonance frequency of 23.5 kHz that is a relatively low frequency, and is therefore large in size. The handpiece 404 can be designed to have a thick long part for clamping a tissue. This is advantageous.

As mentioned above, it is demanded that a plurality of handpieces can be used as therapeutic appliances for the ultrasonic operation system 401 in compliance with various kinds of treatment. The ultrasonic operation system 401 is therefore required to cope with a plurality of frequencies of an output current.

Next, the internal configuration of the main apparatus 402 included in the ultrasonic operation system 401, which is a constituent feature of the present embodiment, will be described in conjunction with FIG. 20.

The configuration includes only components needed to monitor the frequency of an output current. All the other components needed for the ultrasonic operation system are well-known, and the description of the components will be omitted.

Figure 20:
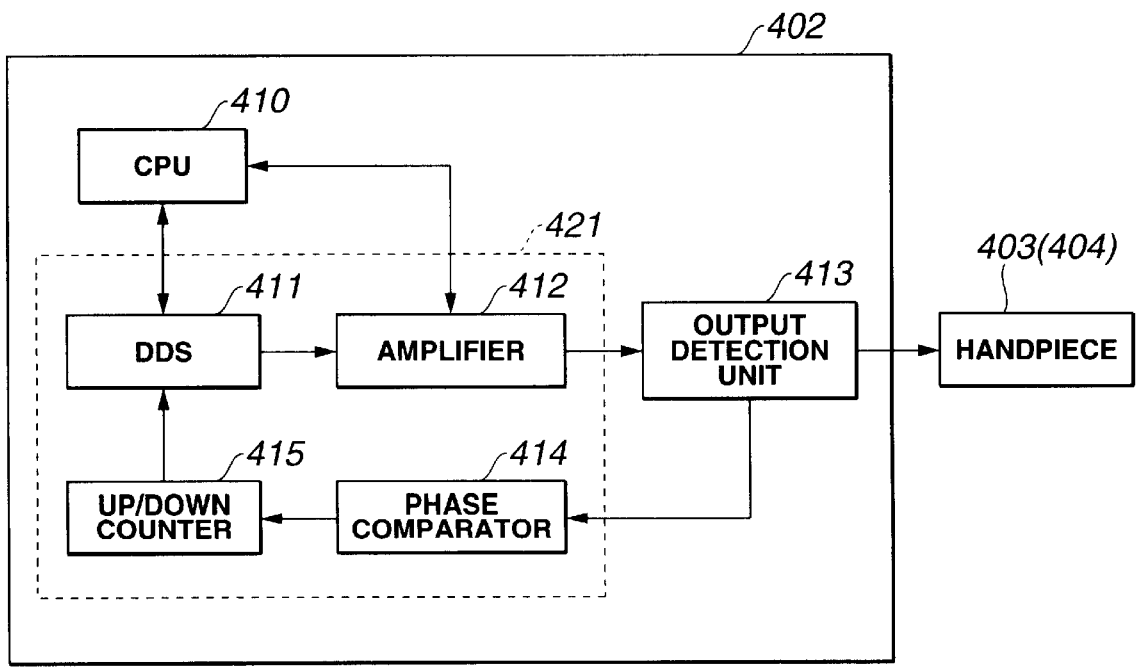

As shown in FIG. 20, in the main apparatus 402, a CPU 410 transmits information of the frequency of an output current to a DDS 411. Based on the information of the frequency of an output signal sent from the CPU 410, the DDS 411 outputs a sine wave, which has the same frequency as the frequency of an output current, to an amplifier 412. Moreover, the CPU 410 outputs information of a set value of an output current to the amplifier 412.

The amplifier 412 amplifies the sine wave output from the DDS 411 to the set value of an output current. Consequently, ultrasonic waves are propagated to the handpiece 403 (or handpiece 404) via an output detection unit 413.

The handpiece 403 (or handpiece 404) exhibits an inherent resonance frequency as mentioned above. If the handpiece is driven at a frequency other than the resonance frequency, the phase of an induced output current does not match the phase of an applied voltage.

The output detection unit 413 detects the phases of the applied voltage and induced current, and outputs the information to a phase comparator 414.

The phase comparator 414 compares the phase of the applied voltage detected by the output detection unit 413 with the phase of the induced current detected thereby, and outputs the result of comparison to an up/down counter 415.

The up/down counter 415 outputs information of an increase or decrease in frequency, which is calculated based on the result of comparison, to the DDS 411.

Thus, an actual output current is locked on to the resonance frequency of the handpiece 403 (or handpiece 404) so that the frequency of the output current will be agreed with the resonance frequency. Moreover, an amplification factor is changed so that the output current will assume a set current value. Eventually, an ultrasonic operation is performed.

Moreover, a unit defined with a dashed line in FIG. 20 corresponds to an analog PLL employed in accordance with a related art. The unit is a digital PLL 211. The digital PLL 221 is normally required to offer a high processing speed, and therefore realized with a high-speed device that is a programmable device such as a DSP or an EPGA.

Figure 21:
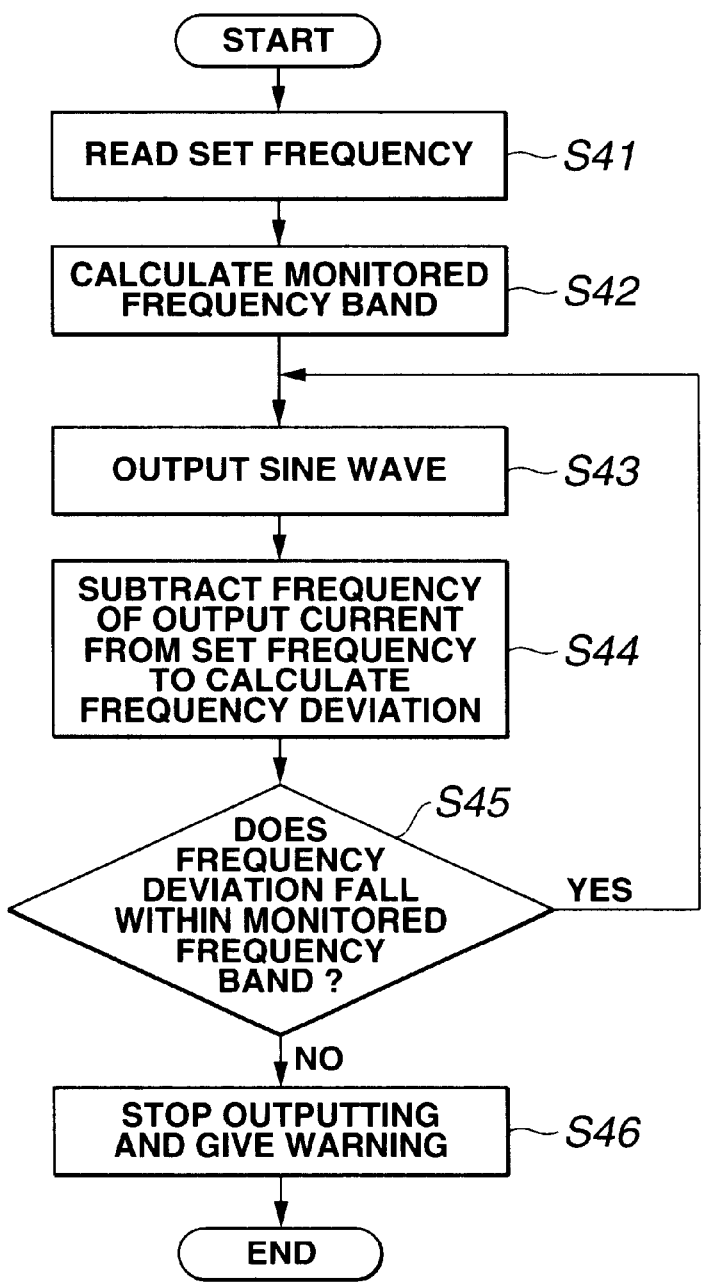

Next, a means for monitoring the frequency of an output current will be described in conjunction with the flowchart of FIG. 21. Herein, a description will be made on the assumption that the monitoring means is incorporated in the DDS 411.

First, at step S41, the DDS 411 reads a set frequency under control of the CPU 410. Normally, an identification resistor is incorporated in the handpiece 403 (or handpiece 404), though it is not illustrated. A voltage proportional to the resistance of the identification resistor is read using a constant-current circuit. Thus, the CPU 410 recognizes the resonance frequency of the handpiece 403 (or handpiece 404).

For recognizing the resonance frequency, the CPU 410 may read information stored in an identification memory, which is incorporated in the handpiece 403 (or handpiece 404), through data communication.

After reading the information of the set frequency, the DDS 411 calculates a monitored frequency band according to the information at step S42. For example, assuming that the handpiece 403 exhibits a resonance frequency of 47 kHz, the monitored frequency band is set to ±2.35 kHz. Assuming that the handpiece 404 exhibits a resonance frequency of 23.5 kHz, the monitored frequency band is set to ±1.175 kHz. The higher the resonance frequency, the wider the monitored frequency band. This is because the performance of a handpiece exhibiting a higher resonance frequency often differs from product to product because of inconsistent handling in the process of manufacturing.

After calculating the monitored frequency band, the DDS 411 outputs a sine wave whose frequency corresponds to the set frequency.

Thereafter, at step S44, a difference between the set frequency and the frequency of an output current is calculated in order to work out a frequency deviation. The frequency of an output current is the frequency of a current output from the DDS 411 which is changed by the up/down counter 415.

At step S45, the calculated frequency deviation is compared with the monitored frequency band. If the frequency deviation falls within the monitored frequency band, control is returned to step S43 of outputting a sine wave, and the above processing flow is repeated.

If the frequency deviation exceeds the monitored frequency band, abnormality is recognized at step S46. Outputting is stopped, and a warning is given in the form of an indication or sound.

Owing to the setup of the digital PLL 421, the frequency of an output current can be recognized in real time, and can be compared with the monitored frequency band. The monitored frequency band can be varied depending on the resonance frequency of a handpiece employed.

In the present embodiment, the DDS 411 judges whether the frequency of an output current falls within the monitored frequency band. Alternatively, the CPU 410 may make the judgment. Nevertheless, the same advantages can be provided. In this case, the aforesaid processing flow is modified so that the information of the frequency of an output current will be transferred from the DDS 411 to the CPU 410 and the CPU 410 will compare the frequency of an output current with the set frequency and thus monitor the frequency of an output current. That is to say, a difference between these cases lies in whichever of the DDS 411 and CPU 410 performs monitoring. Whether the DDS 411 or CPU 410 is employed, the monitoring is digitized. Therefore, there is no difference in the degree of difficulty between monitoring performed by the DDS 411 and monitoring performed by the CPU 410. The difference between the cases is determined with whether the DDS 411 or CPU 410 incurs a load, that is, the degree of dispersion of a load.

When the configuration of the present embodiment is adopted, even if handpieces exhibit different resonance frequencies, a deviation of a frequency of an output current from a set frequency is calculated in order to monitor abnormality.

As described previously, according to the present embodiment, even when various types of handpieces are connected or when a large load is imposed on a probe screwed to a transducer, it can be reliably detected whether the frequency of an output current has become equal to an initial resonance frequency.

Figure 22:
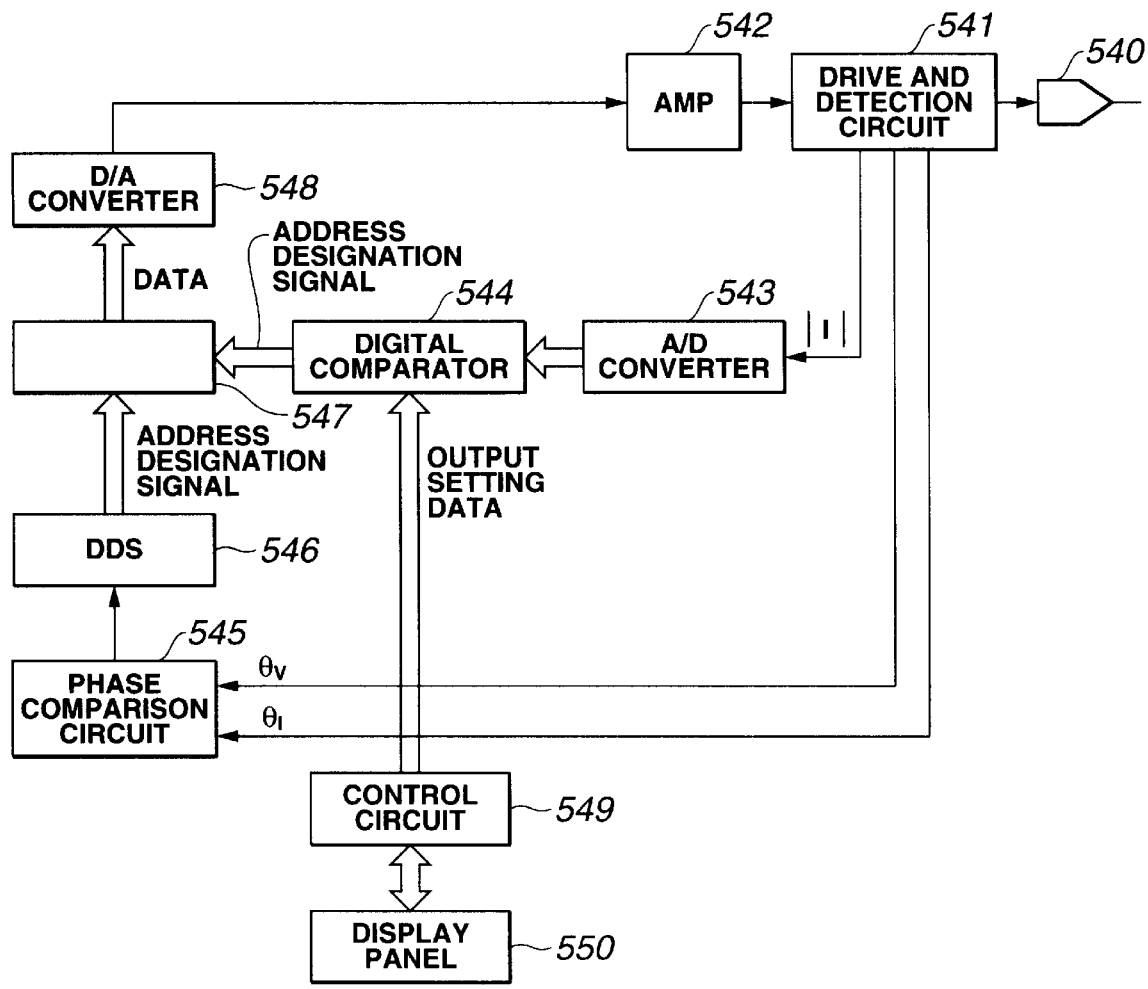
FIG. 22 and FIG. 23 are concerned with a twelfth embodiment of the present invention.

Twelfth Embodiment:

Referring to FIG. 22, an ultrasonic transducer 540 having a probe connected thereto generates ultrasonic oscillations when driven by a drive and detection circuit 541.

An amplifier 542 amplifies an input frequency-change signal to a power level with which the ultrasonic transducer 540 can be driven, and outputs the resultant signal to the drive and detection circuit 541. The drive and detection circuit 541 drives the ultrasonic transducer 540 according to an output of the amplifier 542, and detects a voltage applied to the ultrasonic transducer 540 and an output current induced with the voltage. The drive and detection circuit 541 outputs the phases θv and θI of the voltage applied to the ultrasonic transducer 540 and the induced current to a phase difference detection circuit 545. The phase difference detection circuit 545 detects a difference between the input phases θv and θI.

In the present embodiment, a driving signal is produced using a wave memory 547. An A/D converter 543 receives the absolute value |I| of the induced driving current from the drive and detection circuit 541, converts it into digital data, and outputs the digital data to a digital comparator 544. A control circuit 549 produces output setting data, based on which the amplitude of ultrasonic oscillations to be generated by the ultrasonic transducer 540 is determined, and communicates the data to the digital comparator 544. The digital comparator 544 compares the absolute value of the induced current output from the A/D converter 543 with the output setting data, and designates an address in the wave memory 547 according to a difference between the absolute value and output setting data.

On the other hand, a phase comparison circuit 545 compares the phase of the voltage applied based on the driving signal with the phase of the current induced with the voltage, and outputs the result of comparison to a direct digital synthesizer (DDS) 546. The DDS 546 serves as a digital oscillatory circuit for producing a frequency-change signal whose frequency is changed based on the result of comparison performed by the phase comparison circuit 545. The DDS 546 provides an oscillatory output as an address designation signal that represents an address in the wave memory 547.

The address designation signal output from the digital comparator 544 and the address designation signal output from the DDS 546 are fed to the wave memory 547. Wave data stored in the wave memory 547 is fed to the D/A converter 548. Data items of waves of one cycle exhibiting a plurality of amplitudes are stored in the wave memory 547.

Figure 23:
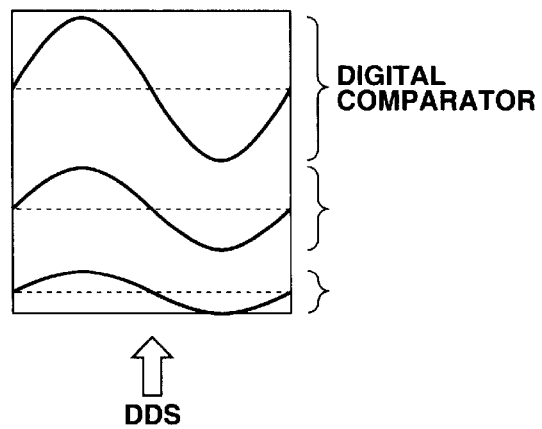
Figure 24:
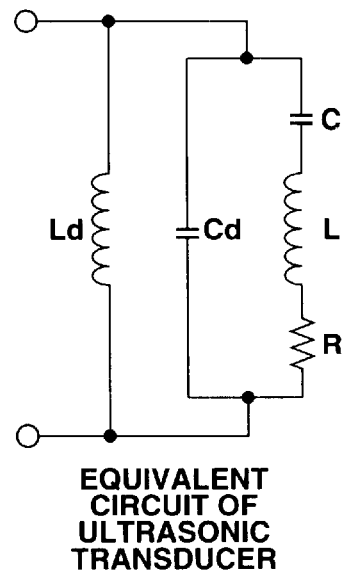
FIG. 24 to FIG. 27 are concerned with a related art.
Figure 25:
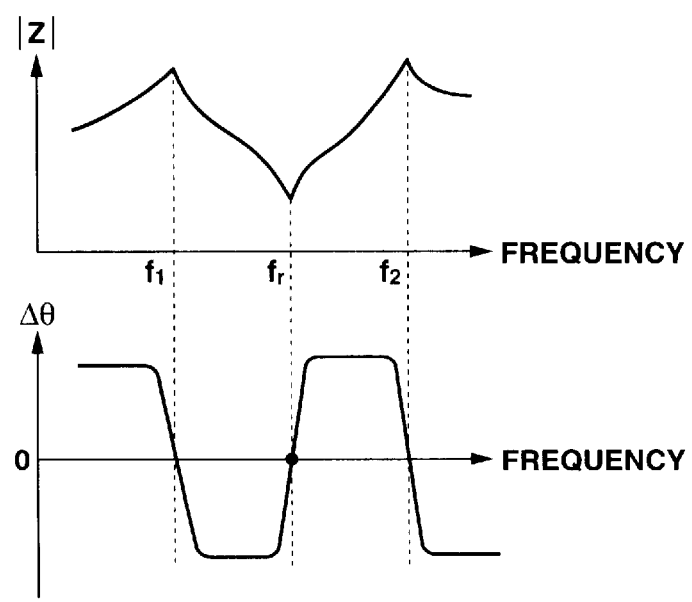
Figure 26:
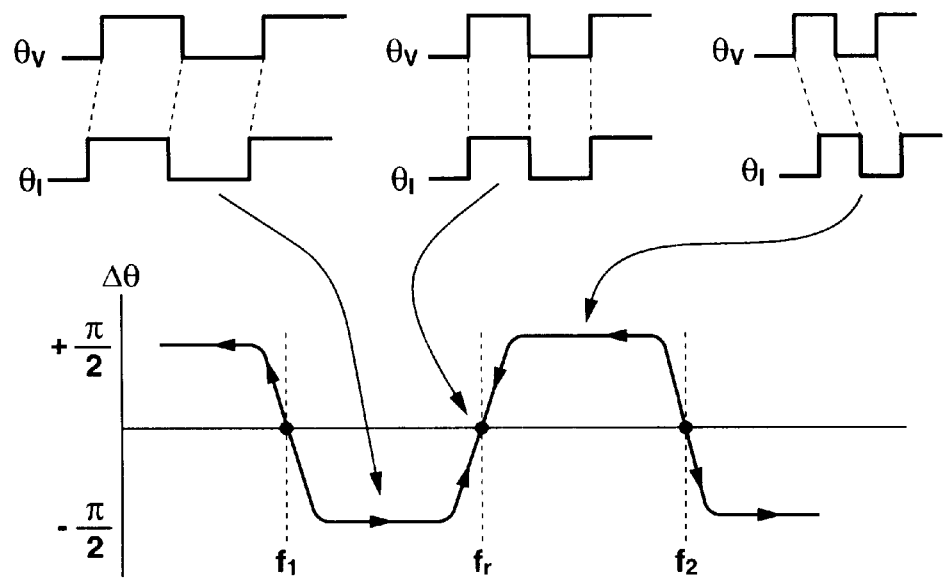
Figure 27:
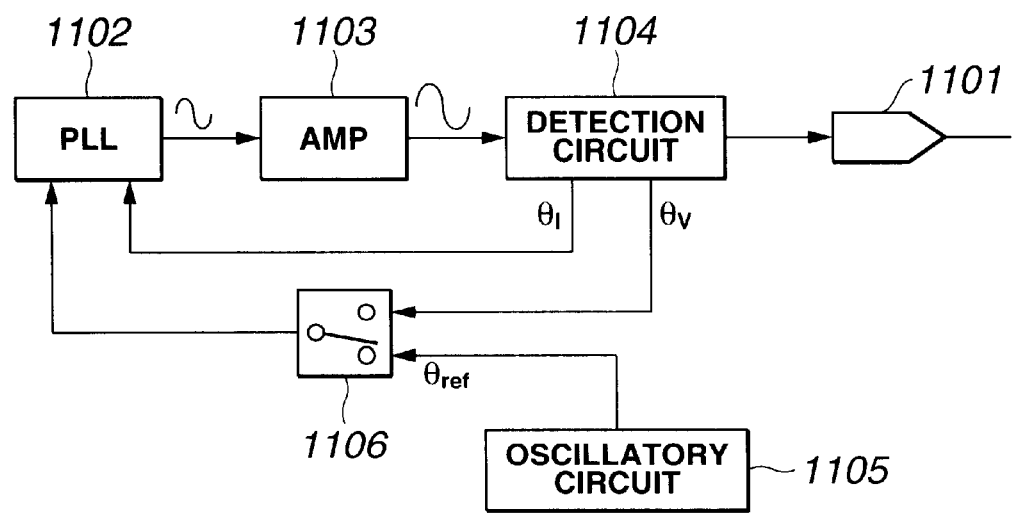

FIG. 23 shows three waves stored in the wave memory 547. The three waves exhibit mutually different amplitudes. Data of a wave specified with the address designation signal sent from the digital comparator 544 from among the three waves is read from the wave memory 547. The wave data read from the wave memory 547 is output at the same frequency as the frequency of the address designation signal sent from the DDS 546.

A D/A converter 548 converts the input wave data into an analog sine wave and outputs the sine wave as a driving signal to the amplifier 542. The control circuit 549 can indicate various kinds of setting information using the screen of a display panel 550.

Next, actions to be performed in the thus-configured present embodiment will be described below.

Wave data read from the wave memory 547 is converted into an analog signal by the D/A converter 548, and amplified by the amplifier 542. Thereafter, the resultant signal is applied to the ultrasonic transducer 540 via the drive and detection circuit 541. The drive and detection circuit 541 communicates the phases θv and θI of a voltage applied to the ultrasonic transducer 540 and an induced current to the phase comparison circuit 545. The drive and detection circuit 541 communicates the absolute value |I| of the induced current to the A/D converter 543.

The A/D converter 543 converts the input absolute value |I| of the induced current into digital data, and outputs the digital data to the digital comparator 544. Meanwhile, the control circuit 549 produces output setting data, with which the amplitude of ultrasonic oscillations is determined, and outputs the data to the digital comparator 544. The digital comparator 544 outputs data, which represents a difference between the two input data items, as address designation data to the wave memory 547. Data of a wave whose amplitude corresponds to the amplitude represented by the address designation data is read from the wave memory 547.

The amplitude of wave data to be read from the wave memory 547 is thus controlled. Thus, a control action for stabilizing the amplitude of ultrasonic oscillations is achieved using the capability of a constant-current circuit realized through digital processing.

On the other hand, the phase comparison circuit 545 outputs a signal, which represents a phase difference between the applied voltage and induced current, to the DDS 546. The DDS 546 produces a frequency-change signal that has its frequency changed based on the phase difference, and outputs the signal as an address designation signal that represents an address in the wave memory 547. Wave data is read from the wave memory 547 according to the frequency of the input frequency-change signal. Consequently, the frequency of a wave represented by wave data to be read from the wave memory 547 changes to nullify the phase difference. Thus, a driving signal is locked onto the resonance frequency of the ultrasonic transducer 540 so that the ultrasonic transducer 540 will be driven at the resonance frequency.

As mentioned above, according to the present embodiment, a control action of controlling the frequency of a driving signal and a control action to be performed using the capability of a constant-current circuit can be digitized. Consequently, the ultrasonic transducer can be driven stably without uncertainty.

According to the present invention, it is apparent that a wide range of different embodiments can be constructed based on the invention without a departure from the spirit and scope of the invention. This invention will be limited to appended claims but will not be restricted to any specific embodiments.

What is claimed is:

1. An ultrasonic operation system comprising:
    a handpiece including an ultrasonic transducer for generating ultrasonic oscillations, and used to treat a living tissue using the ultrasonic oscillations;
    a driving signal oscillator including a frequency data input unit that inputs digital frequency data, and producing a driving signal, based on which said ultrasonic transducer is driven, according to the digital frequency data;
    an amplification circuit for amplifying the driving signal and outputting the resultant driving signal to said ultrasonic transducer;
    a detection circuit for detecting the phase of a voltage applied based on the driving signal to said ultrasonic transducer and the phase of a current induced with the voltage;
    a phase comparison circuit for comparing a signal of the phase of the voltage with a signal of the phase of the current detected by said detection circuit to output a phase difference signal;
    a data transfer circuit for transferring digital frequency initial data which is substantially the resonance frequency of said ultrasonic transducer; and
    an arithmetic circuit for varying to digital frequency initial data transferred from said data transfer circuit according to the phase difference signal from said phase comparison circuit;
    wherein said arithmetic circuit counts the digital data according to the phase difference signal, calculates the digital data counted and the digital frequency initial data, and outputs the result of calculation to said frequency data input unit.

2. An ultrasonic operation system according to claim 1, wherein said arithmetic circuit calculates the digital frequency data by counting pulses.

3. An ultrasonic operation system according to claim 2, further comprising:
    a resonance frequency adjustment circuit for sweeping the frequency of a driving signal at the start of calculation of the digital frequency data so as to agree the frequency of a driving signal with the resonance frequency of said ultrasonic transducer; and
    a control circuit for instructing said arithmetic circuit to set initial frequency data that represents a frequency different from the resonance frequency of said ultrasonic transducer, and to continue counting pulses until the digital frequency data represents the resonance frequency of said ultrasonic transducer.

4. An ultrasonic operation system according to claim 3, further comprising:
    a detection circuit for detecting based on a phase difference between the voltage applied based on the driving signal to said ultrasonic transducer and the induced current whether the frequency of the driving signal has become equal to the resonance frequency of said ultrasonic transducer; and
    a switching circuit for switching said resonance frequency adjustment circuit and said phase comparison circuit according to the result of detection performed by said detection circuit.

5. An ultrasonic operation system according to claim 3, further comprising:
    a gain control amplifier and an output setting circuit for setting a gain to be produced by said gain control amplifier, which are interposed between said driving signal oscillator and said amplification circuit, and
    a sequencer for successively controlling said gain control amplifier and said resonance frequency adjustment circuit.

6. An ultrasonic operation system according to claim 2, further comprising a memory circuit in which the digital frequency data representing the frequency of the driving signal attained when the phase of the voltage applied based on the driving signal matches the phase of the induced current is stored, wherein said arithmetic circuit loads the digital frequency data from said memory circuit at the start of calculation of the digital frequency data.

7. An ultrasonic operation system according to claim 1, further comprising a control circuit for outputting initial frequency data to said arithmetic circuit at the start of calculation of the digital frequency data, wherein said arithmetic circuit starts counting pulses with the initial frequency data set as an initial value so as to thus calculate the digital frequency data.

8. An ultrasonic operation system according to claim 7, further comprising a monitor circuit for monitoring the action of said driving signal oscillator according to the digital frequency data fed to said driving signal oscillator, wherein said monitor circuit sets a specific range in association with the set initial frequency data, and stops the action of said driving signal oscillator when the frequency of a driving signal exceeds the specific range.

9. An ultrasonic operation system according to claim 8, further comprising a notification circuit for performing notification according to the result of monitoring performed by said monitor circuit, wherein said notification circuit notifies the fact that the action of said driving signal oscillator is stopped.

10. An ultrasonic operation system according to claim 1, wherein said handpiece includes a memory means in which initial frequency data associated with said ultrasonic transducer is stored, and said arithmetic circuit adds the initial frequency data to the initial frequency data.

11. An ultrasonic operation system according to claim 1, further comprising a second arithmetic circuit interposed between said phase comparison circuit and said arithmetic circuit, wherein said second arithmetic circuit includes a data converter that converts the result of comparison performed by said phase comparison circuit into frequency change data, and averages a plurality of frequency change data items acquired time-sequentially.

12. An ultrasonic operation system according to claim 11, further comprising an action control circuit for controlling the action of said second arithmetic circuit according to the digital frequency data fed to said driving signal oscillator.

13. An ultrasonic operation system according to claim 1, further comprising a frequency division circuit interposed between said phase comparison circuit and said arithmetic circuit, wherein said frequency division circuit detects a fraction of the frequency of a result-of-comparison signal output from said phase comparison circuit.

14. An ultrasonic operation system comprising
    a plurality of handpieces including ultrasonic transducers that generate ultrasonic oscillations and exhibit different resonance frequencies, and used to treat a living tissue using the ultrasonic oscillations;
    a connector through which said plurality of handpieces are connected;

a discrimination circuit for discriminating the handpieces connected through said connector, a driving signal oscillator including a frequency data input unit that inputs digital frequency data, and producing a driving signal, based on which said ultrasonic transducers are driven, according to the digital frequency data;

an amplification circuit for amplifying the driving signal and outputting the resultant driving signal to said ultrasonic transducer via said connector;

a detection circuit for detecting the phase of a voltage applied based on the driving signal to said ultrasonic transducer and the phase of a current induced with the voltage;

a phase comparison circuit for comparing a signal of the phase of the voltage with a signal of the phase of the current detected by said detection circuit to output a phase difference signal;

an initial frequency data setting circuit for outputting digital initial frequency data which is substantially the resonance frequency of the ultrasonic transducer connected, according to the result of discrimination performed by said discrimination circuit; and an arithmetic circuit for varying the digital frequency initial data transferred from said data transfer circuit according to the phase difference signal from said phase companion circuit;

wherein said arithmetic circuit counts the digital data according to the phase difference signal, calculates the digital data counted and the digital frequency initial data, and outputs the result of said calculation to said frequency data input unit.

15. An ultrasonic operation system according to claim 14, further comprising a monitor circuit for monitoring the action of said driving signal oscillator according to the digital frequency data fed to said driving signal oscillator, wherein said monitor circuit sets a specific range in association with the set initial frequency data, and stops the action of said driving signal oscillator when the frequency of a driving signal exceeds the specific range.

16. An ultrasonic operation system comprising:

a handpiece including an ultrasonic transducer that generates ultrasonic oscillations, and used to treat a living tissue using the ultrasonic oscillations;

an address signal generating circuit including a frequency data input unit that inputs digital frequency data, and producing an address signal whose data transfer rate corresponds to that of the digital frequency data;

a memory in which wave data is stored in advance and from which the wave data is read out based on the address signal;

a D/A converter for converting the wave data read out from said memory into a driving signal to be applied to said ultrasonic transducer;

an amplification circuit for amplifying the driving signal outputted from said D/A converter and outputting the resultant signal to said ultrasonic transducer;

a detection circuit for detecting the phase of a voltage applied based on the driving signal to said ultrasonic transducer and the phase of a current induced with the voltage;

a phase comparison circuit for comparing a signal of the phase of the voltage with a signal of the phase of the current detected by said detection circuit to output a phase difference signal;

a data transfer circuit for transferring digital frequency initial data which is substantially the resonance frequency of said ultrasonic transducer; and an arithmetic circuit for varying the digital frequency initial data transferred from said data transfer circuit according to the phase difference signal from said phase comparison circuit;

wherein said arithmetic circuit counts the digital data according to the phase difference signal, calculates the digital data counted and the digital frequency initial data, and outputs the result of calculation to said frequency data input unit.

17. An ultrasonic operation system according to claim 16, further comprising an address area specification circuit for specifying an address area in said memory, wherein a plurality of wave data items that represent waves of different amplitudes are stored in different address areas in said memory, and said address area specification circuit specifies an address area according to a driving signal to be applied to said ultrasonic transducer.

* * * * *